United States Patent [19]

Kahne et al.

[11] Patent Number: 5,693,769
[45] Date of Patent: *Dec. 2, 1997

[54] GLYCOSYLATED STEROID DERIVATIVES FOR TRANSPORT ACROSS BIOLOGICAL MEMBRANES AND PROCESS FOR MAKING AND USING SAME

[75] Inventors: Daniel Evan Kahne; Suzanne Walker Kahne, both of Princeton, N.J.

[73] Assignees: Transcell Technologies, Inc., Monmouth Junction; Trustees Of Princeton University, Princeton, both of N.J.

[*] Notice: The term of this patent shall not extend beyond the expiration date of Pat. No. 5,571,795.

[21] Appl. No.: 230,685

[22] Filed: Apr. 20, 1994

Related U.S. Application Data

[63] Continuation-in-part of Ser. No. 989,667, Dec. 14, 1992, Pat. No. 5,571,795, which is a continuation-in-part of Ser. No. 806,985, Dec. 13, 1991, Pat. No. 5,338,837.

[51] Int. Cl.$^6$ .................................................. A61K 31/705
[52] U.S. Cl. .................................. 536/5; 514/26; 514/169
[58] Field of Search .......................... 514/26, 169, 170, 514/178, 182; 536/5; 930/10

[56] References Cited

U.S. PATENT DOCUMENTS

| | | | |
|---|---|---|---|
| 3,036,061 | 5/1962 | MacPhillamy | 536/5 |
| 4,150,114 | 4/1979 | Smith | 424/60 |
| 4,260,736 | 4/1981 | Asano et al. | 536/5 |
| 4,360,663 | 11/1982 | Asano et al. | 536/5 |
| 4,522,811 | 6/1985 | Eppstein et al. | 514/2 |
| 4,684,625 | 8/1987 | Eppstein et al. | 514/19 |
| 4,897,355 | 1/1990 | Eppstein et al. | 435/240.2 |
| 4,900,555 | 2/1990 | Cheng et al. | 424/449 |
| 4,902,505 | 2/1990 | Pardridge et al. | 424/85.7 |
| 4,946,787 | 8/1990 | Eppstein et al. | 435/240.2 |
| 4,959,358 | 9/1990 | Carey et al. | 514/171 |
| 4,994,439 | 2/1991 | Longnecker et al. | 514/3 |
| 5,002,936 | 3/1991 | Lieberman et al. | 514/77 |
| 5,049,386 | 9/1991 | Eppstein et al. | 424/427 |
| 5,116,817 | 5/1992 | Anik | 514/15 |
| 5,122,520 | 6/1992 | Azria et al. | 514/171 |
| 5,144,017 | 9/1992 | LaBella et al. | 536/5 |
| 5,192,756 | 3/1993 | Zasloff et al. | 514/182 |
| 5,194,654 | 3/1993 | Hostetler et al. | 558/152 |
| 5,208,036 | 5/1993 | Eppstein et al. | 424/450 |
| 5,264,618 | 11/1993 | Felgner et al. | 560/224 |
| 5,273,965 | 12/1993 | Kensil et al. | 514/3 |
| 5,283,185 | 2/1994 | Epand et al. | 435/172.3 |
| 5,338,837 | 8/1994 | Kahne et al. | 536/5 |
| 5,439,685 | 8/1995 | Augros | 424/430 |
| 5,459,127 | 10/1995 | Felgner et al. | 514/7 |

FOREIGN PATENT DOCUMENTS

| | | |
|---|---|---|
| 0 101 060 | of 1984 | European Pat. Off. . |
| 0 417 725 | 3/1991 | European Pat. Off. . |
| 2 007 410 | 1/1970 | France . |
| 1 527 605 | 10/1978 | United Kingdom . |
| WO 89/02272 | 3/1989 | WIPO . |
| WO 89/08098 | 9/1989 | WIPO . |
| WO 90/11092 | 10/1990 | WIPO . |
| WO 90/14074 | 11/1990 | WIPO . |
| WO 91/16024 | 10/1991 | WIPO . |
| WO A 91/14696 | 10/1991 | WIPO . |
| WO 91/17424 | 11/1991 | WIPO . |
| WO 93/01265 | 1/1993 | WIPO . |
| WO 93/12756 | 1/1993 | WIPO . |
| WO 93/03709 | 3/1993 | WIPO . |
| WO 93/14744 | 8/1993 | WIPO . |
| WO 93/14778 | 8/1993 | WIPO . |
| WO 94/01102 | 1/1994 | WIPO . |
| WO 94/19366 | 9/1994 | WIPO . |
| WO 95/26718 | 10/1995 | WIPO . |

OTHER PUBLICATIONS

Yan, et al, *Journal of the American Chemical Society* "Glysosylation On The Merrifield Resin Using Anomeric Sulfoxides" (1994) p. 6953.

Friedman, T., *Science* (1989) 244:1275–1281.

Felgner, P.L., *Adv. Drug Deliv. Rev.* (1990) 5:163–187.

Nicolau, C., *Proc. Natl. Acad. Sci. USA* (1983) 80:1068–1072.

Felgner, P.L., *Proc. Natl. Acad. Sci. USA* (1987) 84:7413–7417.

Felgner, P.L. and Ringold, G.M., *Nature* (1989) 337:387–388.

Brunette, E., et al., *Nucl. Acids Res.* (1992) 20(5):1151.

Jarnagin, W.R. et al., *Nucl. Acids Res.* (1992) 20(16):4205–4211.

Malone, R.W., *Proc. Natl. Acad. Sci. USA* (1989) 86:6077–6081.

Mannino, R.J. and Gould-Fogerite, S., *Biotechniques* (1988) 6(7): 682–670.

Behr, J.P. et al., *Proc. Natl. Acad. Sci. USA* (1989) 86:6982–6986.

Leonetti, J.P. et al., *Proc. Natl. Acad. Sci. USA* (1990) 87:2448–2451.

Juliano, R.L. and Akhtar, S., *Antisense Research and Development* (1992) 2:165–176.

Legendere, J.Y. and Szoka, Jr., F.C., *Proc. Natl. Acad. Sci. USA* (1993) 90:893–897.

Clark, P.O. and Leach, F.R., *Molec. Gen. Genet.* (1980) 178:21–25.

(List continued on next page.)

*Primary Examiner*—John Kight
*Assistant Examiner*—Howard C. Lee
*Attorney, Agent, or Firm*—Lowe, Price, LeBlanc & Becker

[57] ABSTRACT

Novel glycosylated steroid derivatives for facilitating the transport of compounds across biological membranes, either in admixture or as conjugates, are disclosed. A novel process for efficient synthesis of these glycosylated steroid derivatives, using activated glycosyl sulfoxide intermediates is provided. Methods for the permeabilization of membranes and the enhancement of the activity of predetermined compounds are also provided.

6 Claims, 6 Drawing Sheets

OTHER PUBLICATIONS

Gilboa, E. et al., *Biotechniques* (1986) 4(6):504–511.

Rosenfield, M.A. et al., *Science* (1991) 252:431–434.

Kaneda, Y. et al., *Science* (1989) 243:375–378.

Bellini, A.M. et al., *Arch. Pharm. (Weinheim)* (1990) 323:201–205.

Bellini, A.M. et al., *Eur. J. Med. Chem* (1983) 18(2):185–190.

Bellini, A.M. et al., *Eur. J. Med. Chem* (1983) 18(2):191–195.

Sambrook, J.; Fritsch, E.F.; and Maniatis, T., *Molecular Cloning*, Cold Spring Harbor University Press: Cold Spring Harbor, 1989.

Perrine, T.D. et al., *J. Org. Chem.* (1967) 32:664.

Ferrier, R.J. et al., *Carbohyd. Res.* (1973) 27:55.

Sophia, M.J., *Drug Discovery Today*, "Generation Of Oligosaccharide and Glycoconjugate Libraries for Drug Discovery", vol. 1, No. 1, Jan. 1996, pp. 27–34.

Binns, R., *Drug Discovery Today*, "Challengeability Of Biotechnology Patents in the Light Of Biogen V. Medeva", vol. 1, No. 1, Jan. 1996, pp. 35–38.

Oehlke, J. *Chemical Abstracts*, "CMT–Selectin Syntheses. Preparation Of Deoxycholic ADIC Glucuronides," No. 59167n (1980) vol. 92, p. 714.

Kramer, Werner, et al., *Chemical Abstracts*, "Bile Acid Derivatives, A Process For Their Production And Their Use As Medicines," No. 72019d (1991) vol. 115, p. 842.

Oehlke, J., *Chemical Abstracts*, "Intractions Between Deoxycholic Acid Clucuronides And Blucuronidase," vol. 94 (1981), No. 98644b.

Kahne, Daniel E., et al., *J. Am. Chem. Soc.*, "Glycosylation Of Unreactive Substrates," 111:6881–6882 (1989).

Letsinger, Robert L., et al., *Proc. Natl. Acad. Sci.*, "Cholesteryl–Conjugated Oligonucleotides: Synthesis, Properties, And Activity As Inhibitors Of Replication Of Human Immunodeficiency Virus In Cell Culture," vol. 86 (1989) pp. 6553–6556.

Brown, Dearg S., et al., *Tetrahedron Letters*, vol. 29 (1988) 38:4873–4876.

Dasgupta, Faluni, et al., *Carbohydrate Research*, "Alkyl Sulfenyl Triflate As Activator In The Thioglyscoside–Mediated Formation Of Beta–Glycosidic Linkages," vol. 177 (1988), pp. c13–c17.

Garegg, J. et al., *Carbohydrate Research*, "A Reinvestigation Of Glycosidation Reactions Using 1–Thioglycosides As Clycosyl Donors And Thiophilic Cations As Promoters," vol. 116 (1983), pp. 162–165.

Lonn, Hans, *Carhobydrate Research*, "Synthesis Of A Tri– And A Hepta–Saccharide Which Contain Alpha–L–Fucopyranosyl Groups And Are Part Of The Complex Type Of Carhohydrate Moiety Of Glycoproteins," vol. 139 (1985), pp. 105–113.

Aubin, R. et al. Chapt. 1, Methods in Molecular Biology, vol. 7 (Humana Press), pp. 3–13, (1991).

Nicolaou, K.C., et al., *J. Am. Chem. Soc.*, "A Mild And General Method For The Synthesis Of O–Glycosides," vol. 105 (1983), 8:2430–2435.

Riccio, Raffaele, et al., *J. Org. Chem.*, "Two New Steroidal Glycoside Sulfates, Longicaudoside–A And–B, From The Mediterranean Ophiuroid Ophioderma Longicaudun," 51(4):533–536 (1986).

Oehlke, J., et al. *Pharmazie* (197) 34:383–386; Mitt: Hoppe–Seyler's Z. physiol. Chem. 359, 803 (1978), "Darstellung Von Desoxycholsauregluchuroniden".

Kramer, Werner, et al., *The Journal of Biological Chemistry*, "Liver–Specific Drug Targeting By Coupling To Bile Acids," vol. 267 (1992) 26:18598–18604.

Gordon, G.S., et al., *Proc. Natl. Acad. Sci. USA*, "Nasal Absorption Of Insulin; Enhancement By Hydrophobic Bile Salts," vol. 82 (1985), pp. 741927319–7423.

Cheng, Yuan, et al., *J. Am. Chem. Soc.*, "Facial Amphiphiles," vol. 114 (1992), pp. 7319–7320.

Spigelman, Melvin K., et al., *Neurosurgery*, "Intracarotid Dehydrocholate Infusion: A New Method For Prolonger Reversidble Blood–Brain Barrier Disruption," vol. 12 (1983) 6:606–612.

Malinowska, D.H., et al., *Proc. Natl. Acad. Sci. USA*, "Properties Of The Gastric Proton Pump In Unstimulated Permeable Gastric Glands," vol. 78 (1981) 9:5908–5912.

Andreotti, Amy Hamilton, et al., *J. Am. Chem. Soc.*, "Effects Of Glycosylation On Peptide Backbone Conformation," vol. 115 (1993) 8:3352–3.

Goodchild, John, et al., *Proc. Natl. Acad. Sci. USA*, "Inhibition Of Human Immunodeficiency Virus Replication By Antisense Oligodeoxynucleotides," vol. 85 (Aug. 1988) pp. 5507–5511.

Stein, C.A., et al., *Biochemistry*, "Mode Of Action Of 5'–Linked Cholesteryl Phosphororothioate Oligodexynucleotides Inhibiting Syncytia Formation And Infection By HIV–1 And HIV–2 In Vitro," vol. 30 (1991) 2439–2444.

Marshall, W.S. et al., *Science*, "Phosphorodithioate DNA As A Potential Therapeutic Drug," vol. 259 (1993) 1564–1540.

Caruthers, Marvin H., et al., *Nucleosides & Nucleotides*, "Chemical And Biochemical Studies With Dithioate DNA," vol. 10 (1991) 47–59.

Agrawal, Sudhir, et al., *Nucleic Acid Research*, "Efficient Methods Of Attaching Non–Radioactive Labels To The 5' Ends Of Synthetic Oligodeoxyribonucleotides," vol. 15 (1986) 6227–6245.

Longman, Roger, *In Vivo: The Business and Medicine Report*, "R&D Strategies: The Promise Of Combinatorial Chemical," (May 1994) 23–27, 30–31.

Alper, Joseph, *Science*, "Research News: Drug Discovery On The Assembly Line," vol. 264 (1994) 1399–1401.

Felgner, Philip L., *Focus*, "Cationic Liposome–Mediate Transfection," vol. 11 (1989) 2:21–25.

Benvenisty, Nissim, et al., *Proc. Natl. Acad. Sci. USA*, "Direct Introduction Of Genes Into Rats And Expression Of The Genes," vol. 83 (1986) 9551–9555.

Wu, George Y., et al., *The Journal of Biol. Chem.*, "Communication: Receptor–Mediated Gene Delivery And Expression In Vivo," vol. 263 (1988) 29:14621–14624.

Goodchild, John, *Bioconjugate Chem.*, "Review: Conjugates Of Oligonucleotides And Modified Oligonucleotides: A Review Of Their Synthesis And Properties," vol. 1 (1990) 3:165–187.

Logan, G., et al., "Vascular Permeability Changes In Inflammation: II. The Effect Of Lecithinase Antagonists In Ultraviolet Injury In The Guinea Pig," (1965) 324–330.

Ng, Ronald H., et al., "Failure Of A Phospholipiase A Inhibitor To Inhibit β–Bungarotoxin Phospholipase A," vol. 120 (1977) 577–579.

Rosenthal, Arthur F., et al., *The Journal of Biol. Chem.*, "A Synthetic Inhibitor Of Venom Lecithinase A," vol. 235 (1960) 8:2202–2206.

Budker, Vladimir G., et al., *Antisense Research and Development*, "Cell Membranes As Barriers For Antisense Constructions," vol. 2 (1992) 177–184.

Moss, Robert A., et al., *J. Am. Chem. Soc.*, "Bilayer–Bridging Bolaamphiphilic Lipids," vol. 114 (1992) 9227–9229.

Walker, Christopher, et al., *Proc. Natl. Acad. Sci. USA*, "Cationic Lipids Direct A Viral Glycoprotein Into The Class I Major Histocompatibility Complex Antigen–Presentation Pathway," vol. 89 (1992) 7915–7918.

Moss, Robert A., et al., *Langmuir*, "Comparative Dynamic Stabilities Of Cyclopropyl And Olefinic Model Lipids In Liposomes. A Coordinated Kinetic and Spectroscopic Study," vol. 8 (1992) 1731–1735.

Elbert E., et al., *J. Am. Chem. Soc.*, "Hydrophilic Spacer Groups In Polymerizable Lipids: Formation Of Biomembrane Models From Bulk Polymerized Lipids," vol. 107 (1985) 4134–4141.

Estrada–O., Sergio, et al., *Biochemistry*, "Effect Of Phospholipids On Induced Enzyme Release From Mitochondria," vol. 5 (1966) 3432–3440.

Rosenthal, Arthur F., et al., *Archives of Biochemistry and Biophysics*, "The Inhibition Of Lecithinase D Activity By A Synthetic Lipid," vol. 96 (1962) 240–245.

Moss, Robert A., et al., *Journal of Physical Organic Chemistry*, "Kinetic Evidence For Interdigitation In Model Lipid Bilayers," vol. 5 (1992) 467–470.

Moore, Karen S., et al., *Proc. Natl. Acad. Sci. USA*, "Squalamine: An Aminosterol Antibiotic From The Shark," vol. 90 (1993) 1354–1358.

Ruger, J.–J., et al., *Pharmazie*, "Synthese Einiger Di–O–Hexadecylglycerolderivate Mit Ladungstragern," vol. 35 (1980) H.1.

Moss, Robert A., et al., *Tetrahedron Letters*, "Iodosobenzoate–Functionalized Surfactant Vesicles: Adjustable Reactivity In Reactive Phosphate Cleavage," vol. 30 (1989) 16:2071–2074.

Moss, Robert A., et al., *Tetrahedron Letters*, "Dynamics Of Liposomes Constructed From Phytanyl Lipids," vol. 31 (1990) 52:7559–7562.

Menger, F.M., et al., *J. Org. Chem.*, "Lipid–Catalyzed Transport Of CU(II) Through Liquid Membranes," vol. 58 (1993) 1909–1916.

Hsieh, H.–P., et al., *J. Am. Chem. Soc.*, "Structural Effects In Novel Steriodal Polyamine–DNA Binding," vol. 116 (1994) 12077–12078.

Leonetti, Jean–Paul, et al., *Bioconjugate Chem.*, "Biological Activity Of Oligonucleotide–Poly(L–Lysine) Conjugates: Mechanism Of Cell Uptake," vol. 1 (1990) 149–153.

Osanai, Shuichi, et al., *J. Jpn. Oil Chem. Soc.*, "Preparation of Optically Active Double–Chained Diammonium Cationic Amphiphiles And Their Surfaces And Colloidal Properties," vol. 41 (1992) 293–300.

― □ ― cells in medium (control)
― ■ ― cells in medium + 0.01mM CME
― △ ― cells in medium + 0.32uM TC
― ▲ ― cells in medium + 0.32uM TC + 0.01mM CME
― ○ ― cells in medium + 0.032uM TC
― ● ― cells in medium + 0.032uM TC + 0.01mM CME

Overall Scheme for Synthesis of Synthetic Endorphin

Synthesis of an Endorphin Mimic

GLYCOSYLATED STEROID DERIVATIVES FOR TRANSPORT ACROSS BIOLOGICAL MEMBRANES AND PROCESS FOR MAKING AND USING SAME

This application is a continuation-in-part (CIP) of Application Ser. No. 07/989,667, filed Dec. 14, 1992, now U.S. Pat. No. 5,571,795, which in turn is a CIP of Application Ser. No. 07/806,985, filed Dec. 13, 1991, now U.S. Pat. No. 5,338,837, the complete disclosures of which are incorporated by reference herein.

This invention was made with Government support under Grant No. N0014-91-J-1230, awarded by Office of Naval Research. The Government has certain rights in this invention.

BACKGROUND OF THE INVENTION

The invention is generally directed to novel glycosylated steroid derivatives. These derivatives have a variety of uses, including but not limited to the general permeabilization of membranes, such as biological membranes (e.g., cellular, mucosal, gastrointestinal, blood-brain barrier, and the like). In particular, the present derivatives are useful in facilitating the transport of molecules across biological membranes. The facilitation is achieved by combining the present derivatives with the molecules of interest, either as a conjugate comprising the present derivative covalently linked directly or indirectly with the molecule of interest or as an admixture comprising the two main components. In this manner, the molecule of interest, especially those of a therapeutic significance (more, below) can better exhibit its activity, whether of a biological, physical or chemical nature. The invention is further directed to novel methods for the efficient synthesis of these derivatives, including their combinations with representative molecules of interest.

To elicit the desired biological response, a molecule of therapeutic significance, i.e., those having a diagnostic, prophylactic or therapeutic use (and termed herein "therapeutically-significant-molecule" or "therapeutically-significant-compound"), must be made available in an effective-concentration at its site of action. Many factors determine the concentration of a therapeutically-significant-compound, which ultimately reaches the site of action, including the amount administered, and the extent and rate of the compound's absorption, distribution, biotransformation, and excretion. (Goodman and Gilman, *The Pharmacological Basis of Therapeutics*, 6th Edition, MacMillan Publishing Co., Inc., New York, 1980, pp. 1–39.) The foregoing factors may, in turn, be influenced by the chosen route of administration of the therapeutically-significant-compound.

The most common routes of administration of therapeutically-significant-compounds are parenteral (e.g., intravenous, subcutaneous, and intramuscular) and enteral (oral ingestion), although methods to administer therapeutically-significant-compounds across the skin (e.g., transdermal) or mucosa (e.g., oral, nasal, rectal, vaginal, and the like) also are known. Parenteral methods are considered to be extremely effective, in general, allowing for rapid increases in blood levels of a wide range of therapeutically-significant-compounds. Parenteral methods are advantageous in that they circumvent first-passage hepatic metabolism. However, parenteral administration of a therapeutically-significant-compound can cause pain, irritation, possible tissue damage over the long term, and carries a potential risk of infection. In addition, parenteral methods frequently are inconvenient, particularly those that are restricted to trained medical personnel (e.g., intravenous methods).

Enteral methods are more convenient than parenteral methods, and generally are more economical and acceptable to the recipients. However, orally administered, therapeutically-significant-compounds may be inefficiently absorbed (for example, they may decompose within the gastrointestinal tract or may simply pass through without absorption). Moreover, the time from ingestion to absorption may prohibit effective use in emergency situations. As stated above, certain therapeutically-significant-compounds cannot be orally administered as they are destroyed, prior to reaching their site of action, by the digestive enzymes, acid, and surface-active lipids in the gut. Other therapeutically-significant-compounds are subject to extensive, first-passage hepatic metabolism, rendering them ineffective following oral administration.

Non-parenteral methods which circumvent problems associated with instability of drug preparations in the gut and first-passage hepatic metabolism long have been sought. Administration via transdermal, oral mucosal, rectal, and nasal routes are among the alternatives which have been explored. Such alternatives further include administering the therapeutically-significant-compound orally, but encapsulated in a protective delivery system designed to extrude the contents at a predetermined point in the lower gastrointestinal tract. However, the efficacy of these alternative drug delivery methods often is limited by poor absorption of the therapeutically-significant-compounds at the site of delivery or application.

Effective strategies to enhance absorption of therapeutically-significant-molecules across membranes, such as mucosal membranes, cellular membranes, nuclear membranes, and the like, could enhance the efficacy of many known drug preparations that are poorly absorbed regardless of the method of administration. Such strategies to enhance trans-membrane absorption or penetration could be particularly useful for therapeutically-significant-compounds that are administered across the skin and mucosal tissues, including mucosal tissues of the gastrointestinal, genitourinary, and respiratory tracts.

The basic structural unit of biological membranes is a phospholipid bilayer, in which are embedded proteins of various size and composition. The surfaces of the phospholipid bilayer, which project into the aqueous cellular environment, are formed by the hydrophilic heads of the phospholipids; the interior of the bilayer is comprised of the fatty acyl hydrophobic tails. The membrane proteins may be involved in transport processes and also may serve as receptors in cellular regulatory mechanisms or signal transduction.

Natural mechanisms for traversal of biological membranes include passive diffusion, facilitated diffusion, active transport, receptor-mediated endocytosis and pinocytosis. Passive diffusion works best for small molecules that are lipid-soluble. However, biological membranes are essentially impermeable to most water-soluble molecules, such as nucleosides, amino acids, proteins, and other hydrophilic, therapeutically-significant-molecules. Such molecules enter cells via some type of carriermediated transport system in which specific entities facilitate traversal of the membrane. Natural carriers for facilitating traversal of the membrane are of limited utility, however, as such carriers will accept substrates of only a predetermined molecular configuration. Many therapeutically-significant-compounds are not efficiently absorbed because they are neither lipophilic enough to diffuse passively across cell membranes nor possess the structural features recognized by the natural transport systems.

Strategies to enhance the uptake of therapeutically-significant-molecules across biological membranes have been investigated previously and fall into two broad categories. The first category includes all strategies in which the structure of the therapeutically-significant-compound is changed, either by making the compound itself more lipophilic or by conjugating the compound to other entities known to interact with phospholipid membranes. The common goal has been to increase passive diffusion across the membrane by lowering the energy barrier to diffusion and/or by increasing the local concentration of the compound at the membrane surface.

As mentioned above, the first category includes the strategy of taking advantage of the cellular transport mechanism (either active or facilitated transport or receptor-mediated endocytosis) by conjugating the therapeutically-significant-compound to entities known to interact with the cellular transport machinery. Among the reported techniques to conjugate molecules of therapeutic significance to other entities is the work of Letsinger and others on oligonucleotidecholesterol conjugates. (See, Letsinger RL et al. "Cholesteryl-conjugated oligonucleotides: Synthesis, properties, and activity as inhibitors of replication of human immunodeficiency virus in cell culture." *Proc. Natl. Acad. Sci. USA* (September 1989) 86:6553–6556; Stein C A et al. "Mode of Action of 5'-Linked Cholesteryl Phosphorothioate Oligodeoxynucleotides in Inhibiting Syncytia Formation and Infection by HIV-1 and HIV-2 in Vitro." *Biochemistry* (1991) 30:2439–2444.)

Targeting molecules to the brain requires traversal of the blood-brain barrier, a capillary including system with unique morphological characteristics, which acts as a system-wide cellular membrane separating the brain interstitial space from the blood. Like other biological membranes, the blood-brain barrier is relatively impermeable to many hydrophilic, therapeutically-significant-compounds. The strategies which have been developed for targeting compounds to the brain include direct delivery by invasive procedures, intra-arterial infusion of hypertonic substances, and conversion of hydrophilic compounds to lipid-soluble entities.

U.S. Pat. No. 4,902,505 describes a recent attempt to facilitate transport by coupling a hydrophilic peptide of interest to a peptide carrier which itself is capable of traversing the barrier via receptor-mediated transcytosis.

The second broad category to enhance uptake includes those strategies in which the therapeutically-significant-compound is administered to specific body surfaces as an admixture with other molecules that are known to permeabilize membranes. For example, several investigators have attempted to mix insulin with adjuvants, such as bile salts, which might enhance nasal insulin absorption. (See, Hirai et al. *Int. J. Pharmaceutics* (1981) 9:165–184; Hirai et al. *Diabetes* (1978) 27:296–199; British Patent No. 1,527,506; U.S. Pat. No. 4,153,689; and Pontiroli et al. *Br. Med. J.* (1982) 284:303–386.) EP 0 444 778 describes the use of alkyl saccharides to enhance the penetration of topically applied drugs across mucus-covered epithelial tissues, in general, and the corneal epithelium, in particular. U.S. Pat. No. 4,865,848 to Cheng et al., issued Sep. 12, 1989, discloses the use of sucrose esters, particularly sucrose monolaurate, for enhancing the transdermal flux of transdermally-delivered drugs. U.S. Pat. No. 4,746,508 to Carey et al., issued May 24, 1988, reports the use of fusidic acid and cephalosporin derivatives to increase the permeability of human and animal body surfaces to drugs.

The glycosylated steroid derivatives of the present invention may be used effectively in a strategy for enhancing the uptake of a second compound through a particular membrane, including the two broad categories discussed above. Indeed, it has been discovered that the instant derivatives can interact with a wide variety of membranes, including biological phospholipid membranes, thereby possessing the potential to enhance the penetration of therapeutically-significant-compounds through such membranes.

Like some of the previously used adjuvants and "enhancers" (e.g., cholic acid and fusidic acid derivatives), the novel derivatives of the present invention are amphiphilic in a facial sense; that is, one side or face of the molecule is hydrophobic while the opposite side or face is hydrophilic. However, the novel derivatives of the present invention have structural features which differ significantly from those of the previously known "enhancers". That is, the instant derivatives are glycosylated on the hydrophilic face of the molecule in a manner that is not shared by any previously known, facially-amphiphilic steroid.

The present inventors have discovered that glycosylation on the hydrophilic surfaces significantly changes both the solubility properties of the steroids and the manner in which they associate. Many of the instant glycosylated steroids have been shown by the inventors to be more effective than the parent, nonglycosylated steroids in permeabilizing both artificial and biological membranes. The novel, glycosylated steroid derivatives of the present invention, therefore, have been found to increase the delivery of therapeutically-significant-compounds across a variety of membranes. The enhanced transport is facilitated by combining the instant derivatives with the therapeutically-significant-compounds, either as admixtures or as conjugates therewith.

Prior to the present invention, no method existed for efficiently synthesizing all of the glycosylated steroid derivatives of the present invention. Many glycosylation reactions using thioglycosides have been reported. (See, Ferrier R J et al. "A Potentially Versatile Synthesis of Glycosides," *Carbohydrate Research* (1973) 27:55–61; Gategg P J et al. "A reinvestigation of glycosidation reactions using 1-thioglycosides as glycosyl donors and thiophilic cations as promoters," *Carbohydrate Research* (1983) 116:162–5; Nicolaou K C et al. "A Mild and General Method for the Synthesis of O-Glycosides," *J. Am. Chem. Soc.* (1983) 105:2430–2434; Lonn H. "Synthesis of a tri- and a hepta-saccharide which contain α-L-fucopyranosyl groups and are part of the complex type of carbohydrate moiety of glycoproteins," Research (1985) 139:105–113; Andersson F et al. "Synthesis of 1,2-cis-linked glycosides using dimethyl(methylthio)sulfonium triflate as promoter and thioglycosides as glycosyl donors," *Tetrahedron Letters* (1986) 3919–3922; Brown D S et al. "Preparation of cyclic ether acetals from 2-benzenesulphonyl derivatives: a new mild glycosidation procedure." *Tetrahedron Letters* (1988) 29/38:4873–4876; Ito Y et al. "Benzeneselenenyl triflate as a promoter of thioglycosides: a new method for O-glycosylation using thioglycosides," *Tetrahedron Letters* (1988) 10614; Dasgupta F et al. "Alkyl sulfonyl triflate as activator in the thioglycoside-mediated formation of β-glycosidic linkages during oligosaccharide synthesis," *Carbohydrate Research* (1988) 177:c13–c17.) However, none of these reported methods teach the use of a glycosyl sulfoxide as a glycosylating agent.

Utilization of an activated glycosyl sulfoxide intermediate in a process for glycosylating steroids, has been reported previously by the inventors in an article that appeared in the *J. Am. Chem. Soc.* (1989) 111:6881–2, the entire contents of which are incorporated by reference herein. However, the reported method represents only preliminary results on the glycosylation of steroids of the Formula (I). More specifically, further experimentation in the series has revealed unique reaction conditions that are necessary to achieve the efficient and stereoselective synthesis of glycosylated compounds of the Formula (I). In particular, it has been discovered that the reaction solvent plays a critical role in the stereoselectivity of glycosylation. Using a non-polar, aprotic solvent increases selectivity for alpha (α) glycosidic bond formation while the use of a polar, aprotic solvent such as propionitrile increases selectivity for beta (β) glycosidic bond formation.

The type of sulfoxide used in the glycosylation reaction also affects the outcome of the reaction. For example, it is vital to use the para-methoxy phenyl sulfoxide as the leaving group in the novel process described herein to obtain good yields of beta (β) selectivity in the glycosidic bond formation. The yield of the glycosylation reaction yielding alpha (α) or beta (β) glycosidic linkages also may be increased by using less than one equivalent of triflic anhydride in the glycosylation process.

Finally, the identity of the protecting groups present on the glycosyl donor also have an impact on the stereochemical course of the glycosylation reaction. When the protecting group used is pivaloyl, only beta (β) glycosidic bonds are formed in the glycosylation process, regardless of whether an aprotic, non-polar solvent or an aprotic, polar solvent is used for the reaction. The above-recited factors taken together indicate that one skilled in the art could not have practiced the invention without the detailed further experimentation provided herein.

SUMMARY OF THE INVENTION

The present invention is generally directed to novel, facially-amphiphilic, glycosylated steroid derivatives which have been found to be soluble in both hydrophilic aqueous media and hydrophobic membrane-like environments. These unique solubility properties permit the glycosylated steroid derivatives to facilitate the transport of other molecules across biological membranes, including the blood brain barrier. It is, therefore, contemplated that the glycosylated steroid derivatives of the present invention can be used, either in admixture with the therapeutically-significant-molecules or by being conjugated to such molecules, to enhance delivery of the molecules across body surfaces including, but not limited to, the buccal, sublingual, conjunctival, rectal, gastric, intestinal, endometrial, cervical, vaginal, or colonic epithelium; the oropharynx, ear canal, respiratory tract, nasopharynx, urethra, urinary bladder, and tympanic membrane. Alternatively, the glycosylated steroid derivatives of the present invention may be administered in admixture with the glycosylated steroid derivative/ therapeutically-significant-molecule conjugate (hereinafter referred to as the "derivative-compound-conjugate" or simply "conjugate") to further enhance facilitation of trans-surface and trans-membrane transport.

It is further contemplated that the novel glycosylated steroids of the present invention may be used for the delivery of antiviral agents, systemic insecticides, and herbicides, across plant surfaces; and, for the delivery of contact insecticides and miticides, across arthropod surfaces.

A novel process for obtaining these novel, faciallyamphiphilic, glycosylated steroid derivatives and other glycosylated steroids is also disclosed.

Of particular interest are the steroid derivatives of the general Formula (I):

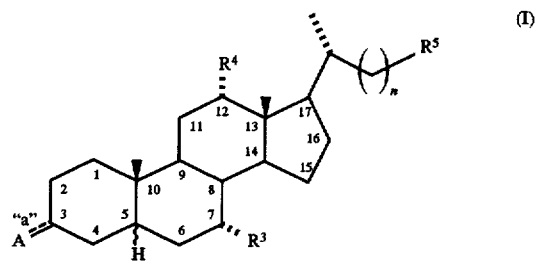

wherein
A is H, O, OH, $OR^6$, $NR^7R^8$, $N_3$, $COR^7$, OCO, O—CO—$OR^9$, O—CO—$R^9$, $NCH_2C_6H_5$, and in which
Ar is phenyl or phenyl substituted with 1–3 groups selected from the group consisting of halogen, $C_1$–$C_{12}$ alkyl or $C_1$–$C_3$ alkoxy;
"a" is a single bond in the alpha or beta configuration with the proviso that when A=O, a is a double bond;
$R^3$ is H, OH or $OR^6$;
$R^4$ is H, OH or $OR^6$;
$R^5$ is $CO_2R^{10}$, $CH_2OR^9$, $CONH_2$, $CONHR^7$, $CONR^7R^8$, CO—S—$R^{10}$, $CH_2S(O)_p$—S—$R^{10}$, $CH_2NH_2$, $CH_2NHR^7$, $CH_2NR^7R^8$, CH2—S(O)p—S—$R^{10}$;
$R^6$ is glycosyl moiety comprising 1–10 monosaccharide units in which the glycosidic linkage at the anomeric carbon atom of each monosaccharide unit is independently alpha or beta;
$R^7$ and $R^8$, independently are H, $C_1$–$C_4$ alkyl, $C_3$–$C_7$ cycloalkyl, C4–$C_{10}$ alkylcycloalkyl, phenyl, benzyl, or, taken together are $(CH_2)_f$ where f=3–6;
$R^9$ is H or $C_1$–$C_3$ alkyl;
$R^{10}$ is H, $C_1$–$C_{10}$ alkyl, $C_1$–$C_{10}$ alkenyl, $C_1$–$C_{10}$ alkynyl, $C_6H_5$ or $CH_2C_6H_5$;
p is 0, 1 or 2;
n is 0, 1 or 2;
or a pharmaceutically-suitable salt thereof. In specific embodiments of the present invention, particular compounds of the Formula (I), in which at least one, preferably two, and most preferably all three of A, $R^3$, and $R^4$ cannot be H, are preferred.

In the instant invention, the monosaccharide is a protected or deprotected sugar residue. For example, the monosaccharide may be a hexose or deoxyhexose selected from the group consisting of D- or L-allose, D- or L-altrose, D- or L-glucose, D- or L-mannose, D- or Lgulose, D- or L-idose, D- or L-galactose, and D- or L-talose. The monosaccharide may further be a protected or deprotected furanose or deoxyfuranose selected from the group consisting of D- or L-ribose, D- or Larabinose, D- or L-xylose and D- or L-lyxose. The protecting groups for the hydroxy groups of the hexoses or furanoses may be any appropriate for the conditions of the contemplated reactions or other use but are preferably selected from the group consisting of benzyl, pivaloyl, trimethylsilyl, tertbutyldimethylsilyl, tertbutyldiphenylsilyl, tri-isopropylsilyl, acetyl, tetrahydropyranyl, benzoyl, $C_1$–$C_3$ alkyl, isopropylidene, benzylidene, (2-methoxyethoxy)methyl, orthoester, paramethoxybenzyl and allyl.

Of further interest are conjugates comprising the compound of Formula (I) covalently linked to a second compound. For example, the second compound can be a therapeutically-significant-compound that is linked directly or indirectly to a compound of Formula (I) via any of the appropriate functional groups present in the compound of Formula (I) which can accommodate a covalent bond, including but not limited to the substituent at C3 (e.g., through any of groups contemplated for or equivalent to "A"), C7 (e.g., through any of groups contemplated for or equivalent to $R^3$), C12 (e.g., through any of groups contemplated for or equivalent to $R^4$) or C17 (e.g., through any of groups contemplated for or equivalent to the side-chain substituent $R^5$). While the identity of the compound of therapeutic significance is limited only by its chemical compatibility with the glycosylated steroid derivatives of the present invention, the following therapeutically-significant-compounds are representative: anti-bacterials such as polyene antibiotics (erythromycin), beta-lactam antibiotics (cefadroxil), and peptide-based or steroidal antibiotics; antifungal agents such as 10-thiastearic acid and 24-thiacholestanol; peptides, polypeptides or proteins, such as regulatory factors, enzymes, antibodies, hormones, and toxins; nucleotides, nucleosides and nucleic acids; and saccharides.

Even though the present invention is not limited by the nature or identity of the second compound that is covalently linked to the compound of Formula (I), certain compounds of Formula (I) are preferred, especially those that contain at least one, preferably two, most preferably three hydroxyl groups. In the conjugates of the present invention, such hydroxyl groups are preferably in an alpha stereochemical configuration. In addition, the hydroxyl groups may bear one or more, preferably two, glycosyl moieties.

It is pointed out that the A and B rings of the steroidal skeleton of the compounds of Formula (I) may be cis or trans to one another, and that the O glycosidic linkage at C7 and C12 may be in the alpha or beta configuration, each independently of the other. Hence, the present invention provides methods for facilitating the transport of any therapeutically-significant-compound across a biological membrane, either in admixture with a glycosylated steroid derivative of the present invention or in the form of a derivative-compound-conjugate. Alternatively, a method is provided for further enhancing trans-membrane transport of the derivative-compound-conjugate by administering the derivative-compound-conjugate in admixture with a glycosylated steroid derivative of the present invention, which may be either the same as, or different from, the derivative of the conjugate.

Also provided are pharmaceutical compositions containing (1) an effective amount of a compound of the Formula (I) and a pharmaceutically-acceptable carrier; (2) an effective amount of a compound of Formula (I), an effective amount of a therapeutically-significant-compound, and a pharmaceutically-acceptable carrier; (3) an effective amount of derivative-compound-conjugate and a pharmaceutically-acceptable carrier; or (4) an effective amount of a compound of Formula (I), an effective amount of derivative-compound-conjugate, and a pharmaceutically-acceptable carrier.

The invention is further directed to a novel process for the efficient synthesis of glycosylated steroid derivatives of the Formula (I) which comprises: allowing a protected glycoside, which is prepared by standard methods well known to those of ordinary skill in the art in which the oxygen atoms at all positions of the sugar, except the anomeric position, are protected with the same or different protecting groups, to react with an —S—R entity under standard conditions, in which R is $C_1$–$C_{10}$ alkyl, pyridyl, furyl, thienyl, phenyl or phenyl substituted with 1–3 groups selected from the group comprising halogen, $C_1$–$C_3$ alkyl, $NO_2$, $C_1$–$C_3$ alkoxy, to yield a protected thio-glycoside; the protected thioglycoside is then allowed to react with meta-chloroperoxybenzoic acid to yield the corresponding sulfoxide derivative; the sulfoxide derivative is then converted to an "activated" intermediate (capable of donating a glycosyl group) using an activating agent, preferably a triflate-containing compound, such as triflic anhydride, methyl triflate or trimethylsilyl triflate; the "activated" intermediate is then contacted with asteroid containing a free hydroxyl group (any other steroid hydroxyl groups which are not to be glycosylated are protected by standard methods) in the presence of 2,6-di-tert-butyl4-methylpyridine in toluene solvent (for formation of alpha,alpha glycosidic linkages) or in propionitrile solvent (for the formation of beta,beta glycosidic linkages), thereby yielding a protected glycosylated steroid, which is then deprotected by standard procedures to yield the glycosylated steroids of the Formula (I).

The oxygen(hydroxyl)-protecting groups utilized may be either electron-withdrawing groups such as esters; or electron-donating groups, such as ethers, including alkyl, silyl, phenyl or benzyl ethers. However, if a pivaloyl ester is used as the protecting group, the resulting glycosidic linkage that is formed is always $\beta,\beta$ regardless of the solvent used for the reaction. The resulting compounds of the invention may be characterized by proton NMR, C-13 NMR, high resolution mass spectroscopy, X-ray crystallography, thin layer chromatography, and the like.

It is also an object of the present invention to provide compounds, compositions, and methods for the transformation of cells, both prokaryotic and eukaryotic. Indeed, by contacting cells with nucleic acids (in any form, including, but not limited to, single-stranged, double-stranded, linear, closed circular, plastmids, vectors, phages, constructs, chromosomes or their fragments) in the presence of selected compounds or conjugates of the present invention, transformed cells can be obtained in which the nucleic acid has been introduced to or incorporated in the cell.

Also provided are methods for the synthesis of the novel derivative-compound-conjugates of the present invention.

Preferred for their ability to permeabilize biological membranes are those compounds of Formula (I) in which A is OH, $OR^6$, O—CO—$R^9$, $OCOC_6H_5$, $OCOC_6H5$-pOMe, $NH_2$; "a" is a single bond; $R^3$ is $OR^6$; $R^4$ is $OR^6$; $R^5$ is $CO_2R^{10}$, $CONR^7R^8$; $R^6$ is a monosaccharide in which the glycosidic linkage at the anomeric carbon atom in the monosaccharide is alpha or beta; $R^7$, $R^8$, and $R^9$ are as defined above; $R^{10}$ is H or $C1$–$C_{10}$ alkyl; and the monosaccharide is a protected or deprotected hexose, such as D- or L-glucose, and further, where the protecting groups are benzyl or pivaloyl.

Preferred for their ability to permeabilize biological membranes are:

(i) 3α-O-benzoyl-trans-5,10-bis-β,β-7,12-glucosyl cholic acid methyl ester;
(ii) 3α-hydroxy-cis-5,10-bis-α,α-7,12-glucosyl cholic acid;
(iii) 3α-hydroxy-cis-5,10-bis-α,α-7,12-glucosyl cholic acid methyl ester;
(iv) 3α-hydroxy-cis-5,10-bis-α,α-7,12-glucosyl-25-tryptophanyl cholic acid;
(v) 3α-ethylcarbonate-cis-5,10-bis-α,α-7,12-glucosyl cholic acid methyl ester;
(vi) 3α-O-benzoyl-cis-5,10-bis-α,α-7,12-glucosyl cholic acid methyl ester;
(vii) 3α-O-p-methoxybenzoyl-cis-5,10-bis-α,α-7,12-glucosyl cholic acid methyl ester;
(viii) 3α-O-benzoyl-cis-5,10-bis-β,β-7,12-glucosyl cholic acid methyl ester;
(ix) 3α-hydroxy-cis-5,10-bis-β,β-7,12-glucosyl cholic acid;
(x) 3α-O-benzoyl-trans-5,10-bis-α,α-7,12-glucosyl cholic acid methyl ester;

(xi) 3α-hydroxy-trans-5,10-bis-β,β-7,12-glucosyl cholic acid; and (xii) 3β-amino-7α,12α-di-(1'-α-glucosyl)-5β-cholic acid methyl ester, its free acid or acid salt forms.

Particularly preferred is compound (g), 3α-O-p-methoxybenzoyl-cis-5,10-bis-α,α-7,12-glucosyl cholic acid methyl ester (CME) and its acid form, 3α-O-p-methoxybenzoyl-cis-5,10-bis-α,α-7,12-glucosyl cholic acid and compound (1)-,3β-amino-7α,12α-di-(1'-α-glucosyl)-5β-cholic acid methyl ester, its free acid or acid salt forms. According to the present invention, a cationic metal salt derivative of the steroid acid is an alkali or alkaline earth metal salt of the acid, including but not limited to sodium, potassium, magnesium, calcium salts, and the like. The ester or amide derivative may be an aliphatic or aromatic ester or amide, although the amide may be a simple amide, i.e., —CONH$_2$. Preferably, the ester or amide is an aliphatic, most preferably a lower alkyl (C$_1$–C$_4$) ester or amide.

DETAILED DESCRIPTION OF THE INVENTION

Figure 1:
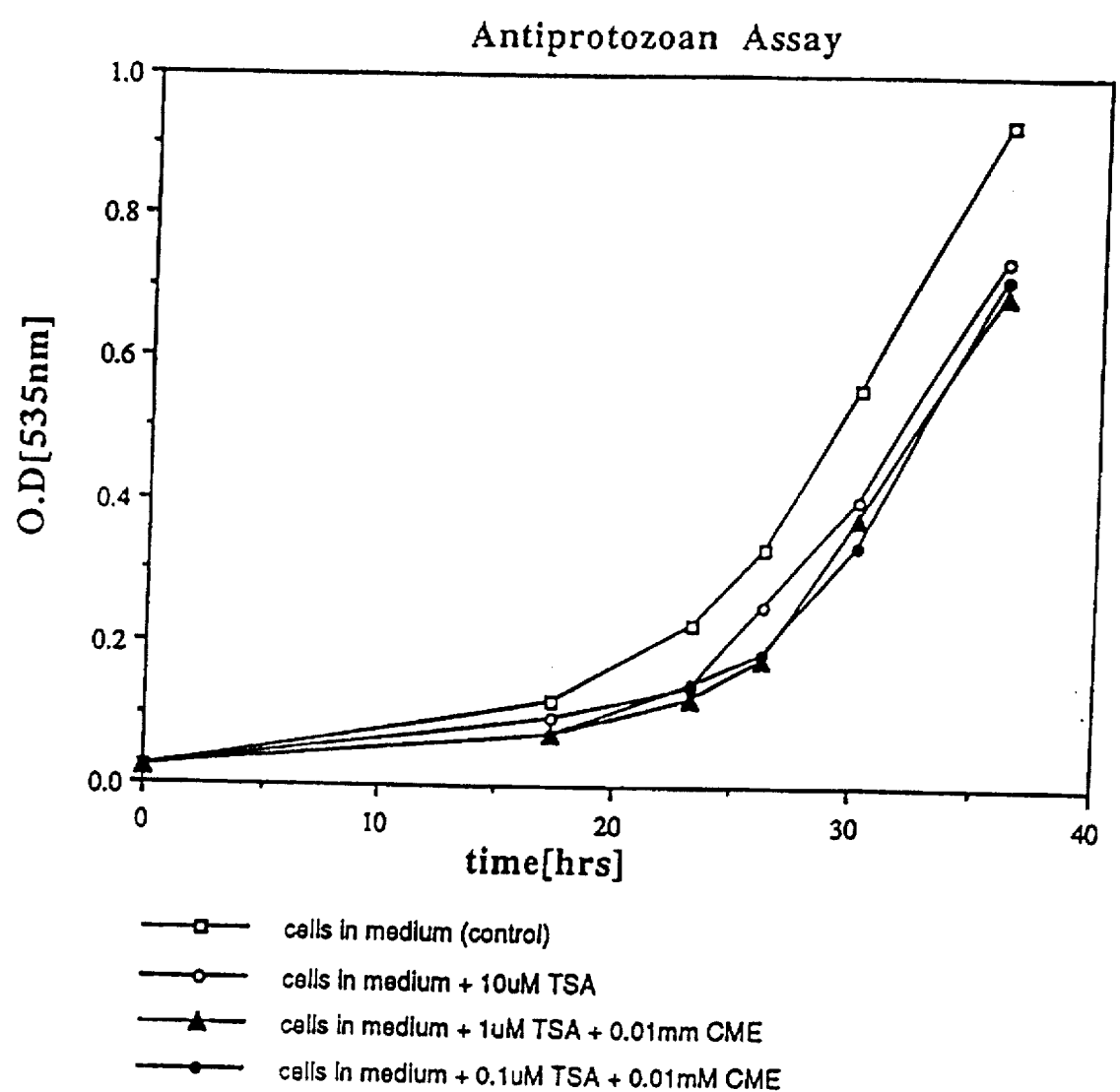
FIG. 1. A graph depicting the enhancing effect of CME, a novel glycosylated steroid derivative of the present invention, on the efficacy of thiastearic acid (TSA), an antifungal agent.

The introduction of molecules of diagnostic, prophylactic or therapeutic interest across body surfaces and/or into cells requires the traversal of one or more semi-permeable biological membranes. The compounds of this invention are useful in permeabilizing biological membranes, thereby assisting body surface and/or membrane transversal of therapeutically-significant-compounds. In one embodiment, the therapeutically-significant-compound is administered in admixture with a glycosylated steroid derivative of the present invention. In another embodiment, trans-surface and/or trans-membrane transport is facilitated by administering the therapeutically-significant-compound in the form of a derivative-compound-conjugate in which the compound of interest is conjugated to the glycosylated steroid, e.g., by linking the therapeutically-significant-compound via the group R$^5$ or by any suitable manner that would be apparent to one of ordinary skill in the art. Further, the derivative-compound-conjugate may be administered in admixture with a novel glycosylated steroid derivative of the present invention, which may be either the same as, or different from, the derivative of the conjugate.

The novel glycosylated steroid derivatives of the present invention may be expected to enhance the therapeutic efficacy of a wide variety of compounds. As a result, many therapeutic applications for the compounds of the present invention may be contemplated. Membrane permeable therapeutic agents could be used in the treatment of a wide variety of illnesses including AIDS and other chronic viral infections, cancer, bacterial and fungal infections, and metabolic diseases such as lupus, diabetes and rheumatoid arthritis.

The ability of the novel glycosylated steroid derivatives of the present invention to interact with, and/or permeabilize, biological membranes, is believed to result from the compounds' facial amphiphilicity. The glycosylated surface of the derivatives is hydrophilic; the non-glycosylated surface is hydrophobic. This facially amphiphilic structure confers unusual properties on the molecules, including an ability to self-associate in both hydrophobic and hydrophilic environments, and to organize at amphiphilic interfaces. Some of the glycosylated steroid derivatives of the present invention have now been shown, by the inventors, to crystallize in layers, with alternating hydrophobic and hydrophilic layers. The non-glycosylated, parent steroid compounds, although possessing some facial amphiphilicity, do not crystallize in register and in organized layers like the glycosylated steroids. In addition, the solubility properties of the glycosylated steroid derivatives of the present invention differ substantially from those of the parent compounds. More particularly, the novel glycosylated steroid derivatives of the present invention, while more soluble than the parent compounds in an aqueous environment are, unexpectedly, not significantly less soluble than the parent compounds in an organic environment.

Based on these observations, the inventors believe (although not wishing to be limited by theory) that the novel glycosylated steroid derivatives of the present invention permeabilize membranes by self-associating to form small, reverse micelies, with their hydrophobic surfaces exposed to the lipids within the membranes. These reverse micelles may function as water-filled pores, allowing therapeutically-significant-compounds to pass through. Alternatively, the presence of these reverse micelles in the membrane may perturb membrane order enough to permit passage of the compounds of therapeutic significance.

Additionally, the compounds of the present invention facilitate the transport of protons or other ions such as Ca$^{2+}$, Na$^+$ or K$^+$ across biological membranes, indicating their use as potential antifungal or antibiotic agents.

The derivative-compound-conjugates of the present invention can be used in vivo, as a component of a pharmaceutical composition in a manner similar to that used for more conventional therapeutic agents. Administration to an individual with a chronic viral infection of the derivative-compound-conjugate comprising an antiviral agent and the glycosylated steroid derivative of the present invention may inactivate the virus by, for example, taking advantage of the antiviral agent's ability to inhibit an enzyme necessary for viral replication. Alternatively, the derivative-compound-conjugate may contain an antisense oligonucleotide sequence such as one known to be effective in inhibiting viral gene function or oncogenic activity. For the individual with a genetic defect, the therapeutically-significant-compound can be a protein that supplements a missing or defective protein or in a gene-therapy approach, introduces a nucleic acid that can supply the missing or defective indigenous gene.

The derivative-compound-conjugate may be administered as a pharmaceutical composition via a variety of routes, including subcutaneous, intravenous, intramuscular, intrasternal, intranasal, intraperitoneal, and intracranial injection or infusion. The pharmaceutical composition also may be administered topically or via inhalation.

More specifically, the compounds of this invention in combination with known therapeutically-significant-compounds, including the derivative-compound-conjugates comprising the compounds of Formula (I), can be administered to prevent, diagnose or treat a whole host of human, veterinary and even plant ailments. Thus, in combination with zidovudine or AZT, currently approved for the treatment of AIDS (or others, such as DDI, which are under development or awaiting regulatory approval) or 1-(2'-deoxy-2'-fluoro-β-D-arabinofuranosyl)-5-iodocytosine (FIAC), 1-(2'-deoxy-2'-fluoro-β-D-arabinofuranosyl)-5-iodouracil (FIAU) or 1-(2'-deoxy-2'-fluoro-β-D-arabinofuranosyl)-5-methyluracil (FMAU), nucleoside analogs useful for inhibiting or arresting a wide range of viral infections (as disclosed, for example, in U.S. Pat. No. 4,594,339, the complete dislcosure of which is incorporated by reference herein), the present invention is useful for the treatment of AIDS and other chronic viral infections, including hepatitis, herpes simplex, and the like.

By judicious choice of therapeutically-significant compound, other medical conditions or ailments can likewise be prevented, diagnosed or treated. Such conditions or diseases include, but are not limited to, autoimmune diseases, such as lupus, rheumatoid arthritis, and diabetes. Other potential indications include cystic fibrosis, cancer and genetic deficiencies, such as growth hormone deficiencies. The compositions of the present invention can be administered by any conventional means available for use in conjunction with pharmaceuticals, either as individual preparations of therapeutic agents or in a combination of more than one therapeutic agent. The compositions can be administered alone, but are generally administered with a pharmaceutically acceptable carrier selected on the basis of the chosen route of administration and standard pharmaceutical practice.

In a preferred embodiment of the present invention, conjugates comprising compounds of the Formula (I) covalently linked to antisense oligonucleotides are contemplated.

Thus, a drug therapy method is contemplated which utilizes glycosteroid-oligonucleotide conjugates for the effective delivery of antisense oligonucleotides across biological membranes. Most preferably bis-glycosylated steroid membrane permeation enhancers are conjugated to antisense oligonucleotide sequences known to inhibit viral (e.g., HIV) replication to provide an effective anti-viral drug therapy. This conjugation is accomplished, for example, by attaching to the oligonucleotide, either by its 5'- or 3'-terminus, to a glycosylated steroid, preferably, via a linker to the steroid C-17 side chain. The new conjugates are found to exhibit an enhanced efficacy to bind to predetermined target sense sequences in a cell as will be shown by both in vitro and in vivo studies. The development of this technology which provides the reliable deliver of antisense oligonucleotides both across cellular and mucosal membranes promises to fulfill the long-awaited anticipated benefits of antisense oligonucleotide drug and gene therapy.

EXPERIMENTAL DESIGN AND METHOD: CONJUGATION OF OLIGONUCLEOTIDES TO GLYCOSYLATED STEROIDS

Several linkers can be introduced at both the 5'- and 3'-ends of the oligonucleotide. Preferably, the chemical synthesis of the oligonucleotide is carried out on a polymer support (e.g., controlled pore glass) in a 3'- to 5'-direction Hence, it is convenient, in this case, to modify the 5'-end. The 3'-end can be modified, of course, but a controlled pore glass support will need to be derivatized accordingly.

The preferred method involves the introduction of an amino linker at either end of the oligonucleotide for subsequent conjugation to the carboxylic acid functionality on the side chain of a glycosylated steroid as shown in scheme 1. Presently, derivatization of the glycosylated steriod is preferably carried out on the C17 side chain because it is suspected that the 3-position (or A ring) of the steroid might be playing a major role in the cell penetration enhancer properties of the glycosylated steroid. It is apparent, however, that conjugation can be accomplished through any substituent that can accommodate a covalent bond (e.g., a substituent on C3, C7, C12, or the side chain substituent on c17).

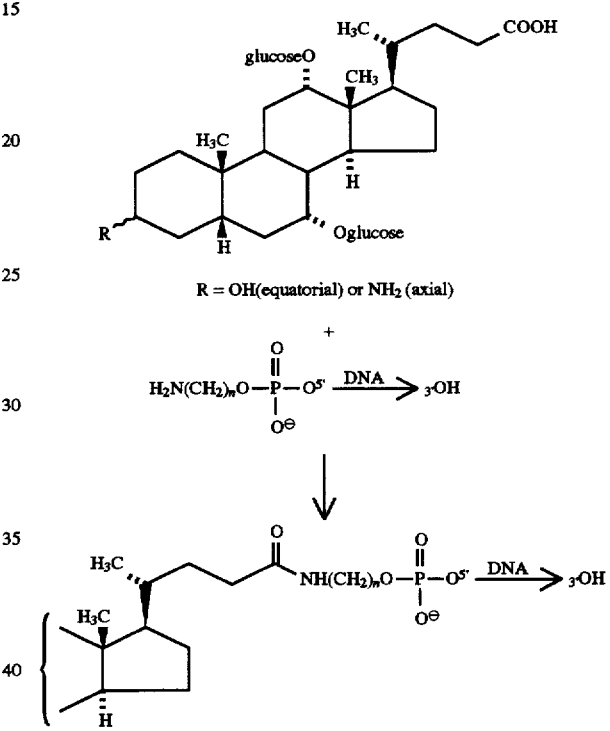

Design Synthesis of an Oligonucleotide Sequence

In view of the results obtained by Zamecnik, Letsinger and Caruthers (See, for example, Goodchild, J. et al. *Proc. Nat'l. Acad. Sci. USA* (1988) 85:5507–5511; Letsinger, R. L. et al. *Ibid.* (1989) 86:6553–6556; Marshall, W. S. and Caruthers, M. H. *Science* (1993) 259:1564–1570, the disclosures of which are incorporated by reference herein) in the use of selective antisense oligonucleotide sequences for inhibition of HIV replication, the following preferred sequences were identified, one corresponding to the primer binding site ("PBS") and the other to the splice acceptor site (5349–5368) of the HIV genome:

| | |
|---|---|
| 5' ACA CCC AAT TCT GAA AAT GG 3' | splice acceptor (SAS) |
| 3' TGT GGG TTA AGA CTT TTA CC 5' | complement |
| 5' AAG TCC CTG TTC GGG CGC CA 3' | primer binding site (PBS) |
| 3' TTC AGG GAC AAG CCC GCG GT 5' | complement |

The splice acceptor sequence and the primer binding site sequence are synthesized with linkers at either the 3'- or 5'-termini. The complements are synthesized without linkers. The complement is synthesized for melting temperature experiments to determine the stability of the duplex before and after conjugation with the glycosylated steroid. The duplex is also desirable for NMR studies to confirm the presence of the amide linkage between the oligonucleotide and the steroid. The syntheses are carried out on an ABI DNA synthesizer using the solid-phase cyanoethylphosphoramidite triester coupling approach developed by Beaucage and Caruthers (S. L. Beaucage, M. H. Caruthers, *Tet. Lett.*, 22, 1859–1862 (1981).) The final dimethoxytrityl ("DMTr") protecting group is left on. The oligonucleotides are then cleaved from the polymer support in NH₄OH at room temperature and fully deprotected after incubation at 55° C. overnight. The hydrophobicity of the dimethoxytrityl protecting group allows easy purification of the desired oligonucleotide by reverse-phase HPLC. The purified oligomer is detritylated and isolated by ethanol precipitation.

An amino linker can be introduced either at the 5'- or 3'-terminus of the oligonucleotide. As stated earlier, because the synthesis of DNA is carried out in a 3'- to 5'-direction (the 3'-end is linked to a polymer support), it is more convenient to introduce an amino linker at the 5'-end of the oligonucleotide. Furthermore, the introduction of the linker can best be carried out using the phosphoramidite chemistry where the commercially available reagents 1 and 2 are used:

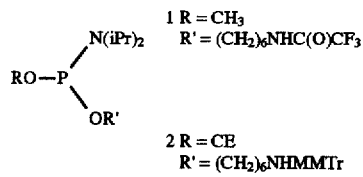

The aminolink 2 reagent (B. J. Bruce, *J. Pharm. Sci.*, 82, 979–987 (1993).) from ABI lacks a protecting group on the amine for easy monitoring of the extent of coupling as well as for purification by RP HPLC. The trifluoroacetyl protecting group is cleaved under the basic conditions required for cleavage of the oligomer from the polymer support. The selective cleavage of the MMTr group while the oligonucleotide is still attached to the polymer support allows conjugation of the glycosylated steroid using solid-phase chemistry.

Several other reagents have been used by different researchers over the years. The length of the linker between the amino functionality and the glycosylated steroid may be varied. Reagent 3 might be of interest for that purpose. It is synthesized using the chemistry summarized in Scheme 2.

SCHEME 2

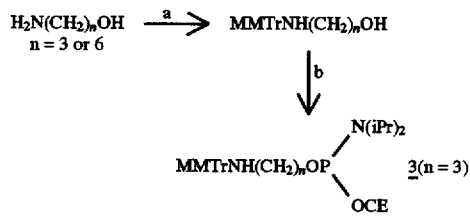

a = MMTrCl (or DMTrCl)/pyridine
b = (iPr)₂NP(Cl)(OCE)/Hunig's base/CH₂Cl₂

The introduction of an amino functionality at the 3'-terminus of an oligonucleotide requires the functionalization of the controlled pore glass (CPG) polymer support. Suitable procedures are known (See, for example, U. Asseline, N. T. Thuong, *Tet. Lett.*, 31, 81–84 (1990) and U. Asseline, E. Bonfils, R. Kurfurst, M. Chassignol, V. Roig, N. T. Thuong, *Tetrahedron*, 48, 1233–1254 (1992)) for functionalization of the support allowing introduction of an amine functionality. The functionalization of the support can be carried out as summarized in Scheme 3.

SCHEME 3

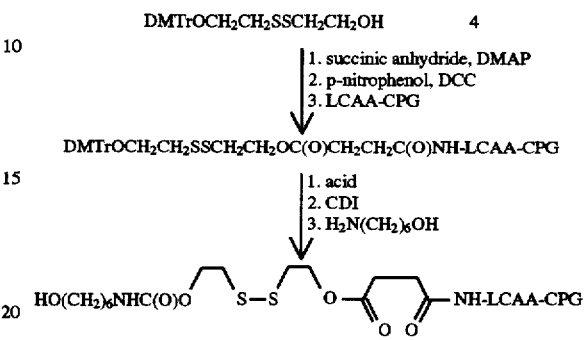

The functionalization of the support can also be accomplished using a modified procedure developed by Damha and co-workers (M. J. Damha, P. A. Giannaris, S. V. Zabarylo, *Nucl. Acids Res.*, 18, 3813–3821 (1990)) which involves reaction of succinic anhydride with the polymer support and subsequent reaction with compound 4 in the presence of DEC. After functionalization of the support, the oligonucleotide is then synthesized using the cyanoethylphosphoramidite triester coupling approach.

It is found that upon treatment with DTT-NH₄OH at the end of the synthesis, both the cleavage of the disulfide bridge and elimination of ethylenesulfide and carbon dioxide occurs (See Scheme 4) to afford the free amino group together with the removal of the cyanoethyl group from the internucleotide phosphate and the acyl groups from the nucleic base. This method for introduction of an amino functionality at the 3'-terminus of an oligonucleotide will generate the same type of linkage that was introduced earlier at the 5'-end of an oligonucleotide. This similarity allows us to directly compare the permeation enhancer properties of conjugated glycosylated steroid-oligonucleotide whether the linkage is at the 3'- or 5'-terminus of the oligomer.

SCHEME 4

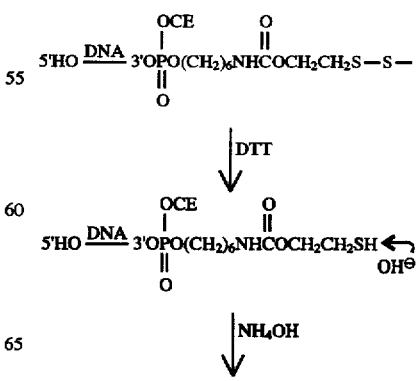

-continued
SCHEME 4

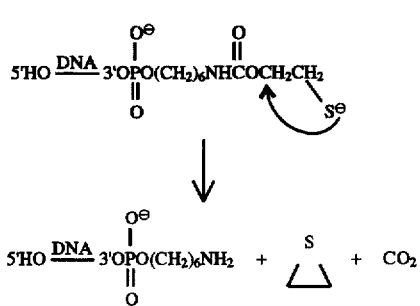

The conjugation of a glycosylated steroid to an amino-linked oligonucleotide can be carried out two ways: conjugation in solution or on a polymer support. Several reports have been published in the literature regarding the conjugation of biotin to oligonucleotides in solution (S. Agrawal, C. Christodoulou, M. J. Gait, Nucl. Acids Res., 14, 6227-6245 (1986); L. Wachter, J-A. Jablonski, K. L. Ramachandran, Nucl. Acids Res., 14, 7985-7994 (1986); J. M. Coull, H. L. Weith, R. Bischoff, Tet. Lett., 27, 3991-3995 (1986); R. K. Gaur, Nucleosides and Nucleotides, 10, 895-909 (1991).) Thus, the N-hydroxysuccinimide derivative of biotin dissolved in DMF and the oligonucleotide dissolved in HEPES or Tris-HCl buffer are mixed together and stirred at room temperature from 1 to 24 hours. The resulting product is purified by RP (i.e., reverse phase) HPLC. One report has also been published on the conjugation reaction carried out on a polymer support (B. D. Gildea, J. M. Coull, H. Koster, Tet. Lett., 31, 7095-7098 (1990)).

To achieve conjugation on a polymer support, the amino-linked oligonucleotide is prepared preferably using the Peninsula Labs reagent in which a MMTr group is present on the amino functionality. The oligonucleotide (still linked to CPG) is detritylated and treated with the N-hydroxysuccinimide derivative of the steroid of interest in $CH_3CN/DIEA/H_2O$ (8/1/1, v/v/v) (Scheme 5). The resulting product is cleaved off of the support and deprotected in $NH_4OH$ at 55° C. overnight.

To achieve conjugation in solution, the amino-linked oligonucleotide is synthesized using either the aminolink 2 reagent or the Peninsula Labs reagent. Using the aminolink 2 reagent, one needs to be able to achieve conjugation on the reaction mixture generated from the final deprotection of the synthesized oligonucleotide since the purification of that amino-linked oligonucleotide can only be achieved by anion-exchange HPLC with difficult separation from the failure sequences. Using the Peninsula Labs reagent, one can use the MMTr group for purification of the amino-linked oligonucleotide by RP HPLC prior to conjugation to the desired steroid. Using this solution phase method, one removes excess DMF, followed by desalting prior to purification by RP HPLC, especially on a large scale.

If one carries out conjugation on a polymer support, filtration of the reagents followed by deprotection in $NH_4OH$, only requires concentration of the ammonium hydroxide solution prior to purification. Thus, the solid-phase conjugation results in a much easier work-up.

SCHEME 5

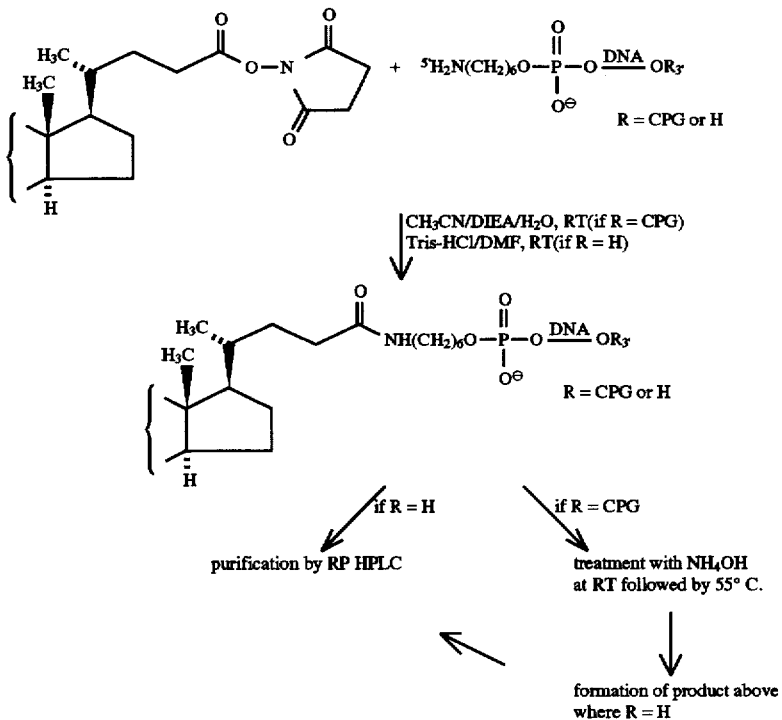

The N-hydroxysuccinimide derivative of the steroids of interest are synthesized as shown in Scheme 7. Cholic acid methylester, its analogs and their glycosylated derivatives are treated with NaOH in order to generate the acid. The acid is then treated with N-hydroxysuccinimide in DMF in the presence of DCC to yield the desired activated acid (J. M. Becker, M. Wilchek, *Biochim. Biophys. Acta*, 264, 165–170 (1972).) The N-hydroxysuccinimide derivatives are then conjugated to the 5'-amino-linked oligonucleotide, preferably using solid-phase chemistry. If the $NH_2$ group of analog (xii) is a problem during coupling, it can be protected with a BOC group which can be cleaved under acidic conditions at the end of the synthesis. The same protocol can be used for any other cell penetration enhancers of the present invention.

SCHEME 6

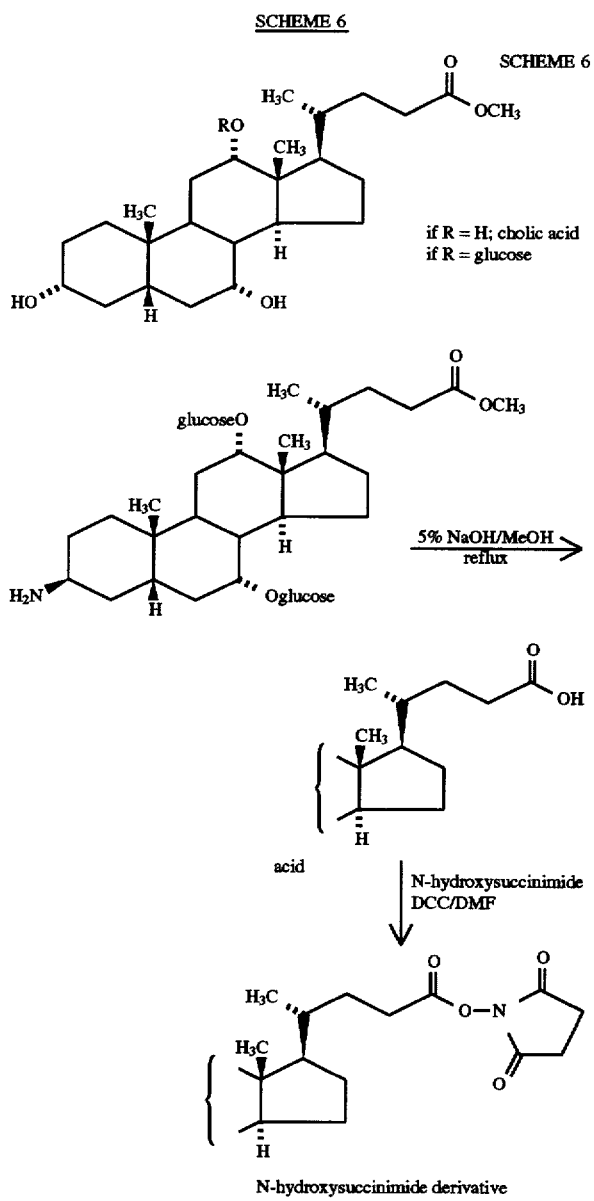

The conjugation of the 3'-amino linked oligonucleotide with the glycosylated steroids can only be accomplished in solution. However, the desired amino-linked oligonucleotide can easily purified by RP HPLC because of the presence of the DMTr group at the 5'-end. The conjugation reaction can then be carried out in solution and the desired conjugated species purified by RP HPLC. Since the amino linker is present in all failure sequences, purification prior to conjugation will be advisable.

MELTING TEMPERATURE EXPERIMENTS AND STABILITY STUDIES

The stability of the duplex can be studied via melting temperature experiments to determine what effect the conjugated glycosylated steroid has on antisense-sense oligonucleotide recognition (See, for example, R. L. Letsinger, G. Zhang, D. K. Sun, T. Ikeuchi, P. S. Sarin, *Proc. Natl. Acad. Sci.(USA)*, 86, 6553–6556 (1989).) The following compounds are presently of interest:

Compound 1: SAS sequence+complement (duplex)

5' ACA CCC AAT TCT GAA AAT GG 3'

3' TGT GGG TTA AGA CTT TTA CC 5'

Compound 2: 5'-amino linked SAS sequence+complement (duplex)

5' $H_2N$ $(CH_2)_6OP(O)_2$ ACA CCC AAT TCT GAA AAT GG 3'

3' TGT GGG TTA AGA CTT TTA CC 5'

Compound 3: cholic acid-SAS conjugated species

Compound 4: Analog iii-SAS conjugated species

Compound 5: Analog xii-SAS conjugated species

Compound 6: PBS sequence+complement (duplex)

5' AAG TCC CTG TTC GGG CGC CA 3'

3' TTC AGG GAC AAG CCC GCG GT 5'

Compound 7: 5'-amino linked PBS sequence+complement (duplex)

5' $H_2N(CH_2)_6OP(O)_2$AAG TCC CTG TTC GGG CGC CA 3'

3' TTC AGG GAC AAG CCC GCG GT 5'

Compound 8: cholic acid-PBS conjugated species

Compound 9: Analog iii-PBS conjugated species

Compound 10: Analog xii-PBS conjugated species

Compounds 3, 4, 5, 8, 9, and 10, above, are used in the duplex form for melting temperature experiments. The presence of the glycosylated steroid on the oligonucleotide does not significantly affect the stability of the duplex as indicated by the absence of significant changes in melting temperature. Compounds 3, 4, 5, 8, 9, and 10, all single-stranded, are further tested in an antiviral assay and in their enhanced ability to cross cell membranes.

Using several commercially available nucleases, the stability imparted by the conjugate to the oligonucleotide is tested.

DOSAGE AND DOSAGE FORMS

The dosage administered will, of course, vary depending upon known factors such as the pharmacodynamic characteristics of the particular prophylactic, diagnostic or therapeutic agent; its mode and route of administration; age, health, and weight of the recipient; nature and extent of symptoms; kind of concurrent treatment; the frequency thereof; and the effect desired. Typically, however, a daily dosage of therapeutically-significant-compound can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results. Still in other situations, a low dose of about 0.1 to about 5 mg, preferably about 0.25 to about 0.75 mg, administered once or twice a day regardless of the weight of the subject may be more appropriate.

Dosage forms (compositions) suitable for internal administration contain from about 1 milligram to about 500 milligrams of therapeutically-significant-compound per unit. In these pharmaceutical compositions the therapeutically-significant-compound ordinarily will be present in an amount of about 0.5–95% by weight based on the total weight of the composition. In the low dosage use, single dose units containing about 0.1 to about 1 mg, preferably about 0.25 to about 0.5 mg, of active ingredient are also provided.

The compositions can be administered orally in solid dosage forms, such as capsules, tablets, and powders, or in liquid dosage forms, such as elixirs, syrups, and suspensions. The compositions also can be administered parenterally, in sterile liquid dosage forms, by inhalation in the form of a nasal spray or lung inhaler, or topically as an ointment, cream or lotion.

Gelatin capsules additionally may contain powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of therapeutically-significant compound over a period of hours. Compressed tablets can be sugar-coated or film-coated to mask any unpleasant taste and protect the tablet from the atmosphere, or enteric-coated for selective disintegration in the gastrointestinal tract and, preferably, within a predetermined section thereof.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration additionally may contain suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl or propyl-paraben, and chlorobutanol.

EXAMPLES

The compounds of Formula (I) can be prepared according to the process shown in Scheme A.

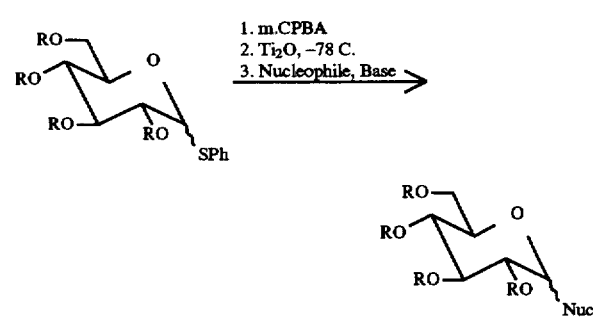

A protected thioglycoside is oxidized with m-chloroperoxybenzoic acid under standard conditions to yield the corresponding sulfoxide. Triflic anhydride (Aldrich) is then added to a solution of the protected glycosyl sulfoxide in toluene at –78° C. followed by the addition of an acid scavenger such as 2,6-di-tert-butyl4-methyl pyridine (Aldrich Chemical Co.) in toluene and the nucleophile dissolved in toluene at –78° C. After stirring for 15–30 minutes, the reaction was removed from the cold-bath and stirred for an additional 10 minutes and quenched by pouring the mixture into aqueous sodium bicarbonate and the protected adduct was isolated by chromatography. Deprotection of the adduct under standard conditions yields compounds of the Formula (I). The appropriate thioglycoside is obtained via standard protection of a selected sugar followed by thioglycoside formation according to methods described above. Via this method, bis-glycosylation of asteroid derivative of the Formula (I) where $R^3$ and $R^4$ are OH selectively produces $\alpha,\alpha$ glycosidic linkages with the glycosyl donor, except where the protecting group used is pivaloyl, in which case only $\beta,\beta$ glycosidic linkages are formed regardless of the solvent used for the reaction.

Alternatively, the protected glycosyl sulfoxide, nucleophile and pyridine base are dissolved in propionitrile at –78° C., followed by the addition of triflic anhydride at –78° C. and the product is isolated as described above. Via this method, glycosylation of asteroid derivative of the Formula (I) where $R^3$ and $R^4$ are OH selectively produces $\beta,\beta$ glycosidic linkages with the glycosyl donor. It is vital to use the p-methoxy phenyl sulfoxide as the leaving group in the above process to obtain the $\beta,\beta$ selectivity in the glycosylation.

The compounds of this invention and their preparation are illustrated further in the following examples. All temperatures are in degrees Centigrade and parts and percentages by weight. In these Examples, unless otherwise indicated, the reactions were performed under an atmosphere of dry argon; "isolation by extraction" refers to the liquid-liquid extraction of a water containing mixture with an indicated solvent, followed by drying the organic phase over sodium sulfate, filtering, and evaporating the solvent under reduced pressure; chromatography refers to the method of medium pressure column chromatography described by W. C. Still, et al. *J. Org. Chem.* (1978) 43:2923.

Example 1 (Part A): Perbenzylated-3α-ethylcarbonatecis-5,10-bis-α,α-glucosyl cholic acid methyl ester.

A 100 ml round bottom flask containing a Teflon® stir bar is flame dried and cooled to –78° C. (acetone/dry ice bath) under argon. 2,3,4,6-tetra-Obenzyl glucose sulfoxide (2.97 g, 4.57 mmol, 4.0 eq.), $C_3$-ethylcarbonate cholic acid (0.563 g, 1.14 mmol, 1.0 eq.) and 2,6-di-tert-butyl-4-methylpyridine (0.936 g, 4.57 mmol, 4.0 eq.) are each dried by azeotroping each separately three times with toluene (15.0 ml). Triflic anhydride (824 µl, 4.57 mmol, 4.0 eq.) is added to the glycosyl sulfoxide dissolved in toluene (5.0 ml) at –78° C. To this mixture is then added the pyridine base in toluene (5.0 ml). After five minutes, the cholic acid derivative, dissolved in methylene chloride (1.0 ml) and toluene (5.0 ml) is added. The reaction is allowed to stir at –78° C. for thirty minutes and then removed from the dry ice bath. After ten minutes, the reaction is quenched by the addition of saturated sodium bicarbonate and the product is isolated by extraction with methylene chloride and purified by flash chromatography on silica gel to provide the title compound (60%) as an oil, $R_f$=0.3 (20% ether/$CH_2Cl_2$).

Example 1 (Part B): 3α-ethylcarbonate-cis-5,10-bis-α,α-glucosyl cholic acid methyl ester Palladium hydroxide (0.030 g, 15% by weight) is added to a mixture of the product of Part A (0.220 g, 0.014 mmol, 1.0 eq.) dissolved in benzene (4.0 ml) and methanol (32.0 ml) at room temperature. The mixture is hydrogenated at 50 psi for 48 hours. The product is filtered through Celite®

(diatomaceous silica, Johns-Manville Corp.) under nitrogen. The solvent is evaporated, and the oil is flash chromatographed with 10% methanol/methylene chloride. To remove the silica gel that dissolves under elution conditions, the product is run through on a reverse phase LH-20 column using methanol as an eluent. The solvent is evaporated to yield the title compound (65%) as a white powder, $R_f$=0.3 (15% MeOH/CH$_2$Cl$_2$), NMR (CDCl$_3$ 500 MHz) δ:5.04 (m, 1H, anomeric β-H), 4.82 (m, 1H, anomeric β-H).

Example 2: 3α-benzoyl-cis-5,10-bis-β,β-glucosyl cholic acid methyl ester 2,3,4,6-tetra-O-benzyl p-methoxy glucose sulfoxide (1.012 g, 1.45 mmol, 4.0 eq.), C3-O-benzoyl cholic acid methylester (0.191 g, 0.364 mmol, 1.0 eq.) and 2,6-di-tert-butyl-4 methyl pyridine (0.179 g, 0.874 mmol, 2.4 eq.) are azeotroped together three times from toluene 20 ml). After removing the toluene under reduced pressure for the last time, the mixture is dissolved in freshly distilled propionitrile and cooled under argon in a dry ice/acetone bath at −78° C. Triflic anhydride (244 μl, 1.45 mmol, 4.0 eq.) is added and the reaction mixture is stirred at −78° C. for 40 minutes. The reaction vessel is removed from the ice bath and stirred for an additional 10 minutes. The reaction is quenched by pouring it into saturated sodium bicarbonate and the product is isolated by extraction with methylene chloride and purified by flash chromatography on silica gel. Catalytic hydrogenation to remove the benzyl protecting groups is accomplished as described above to yield the title compound (60%) as an oil, $R_f$=0.3 (15% MeOH/CH$_2$Cl$_2$), NMR (CDCl$_3$ 500 MHz) δ:4.36 (d, 1H, J=7.92Hz, anomeric-α-H), 4.37 (d, 1H, J=7.92Hz, anomeric-α-H).

Example 3: 2,3,4,6-Tetra-O-benzyl-α-D-glucopyranose (2)

Methyl-α-D-glucopyranose (100 g, 0.516 mol) is suspended in benzyl chloride (400 mL, 3.5 mol) with KOH pellets (336 g, 6 mol), and the mixture is stirred using a mechanical stirrer at 120°–130° C. for 3 h, as shown in Scheme B. The reaction mixture is cooled and water (800 mL) is added to dissolve the crystalline mass, which is extracted with ether (2×200 mL). The combined organic layer is washed with water (2×500 mL) and dried (Na$_2$SO$_4$). The solvents are removed by vacuum distillation to give the crude methyl 2,3,4,6-tetra-O-benzyl-α-D-glucopyranoside for the next reaction.

SCHEME B

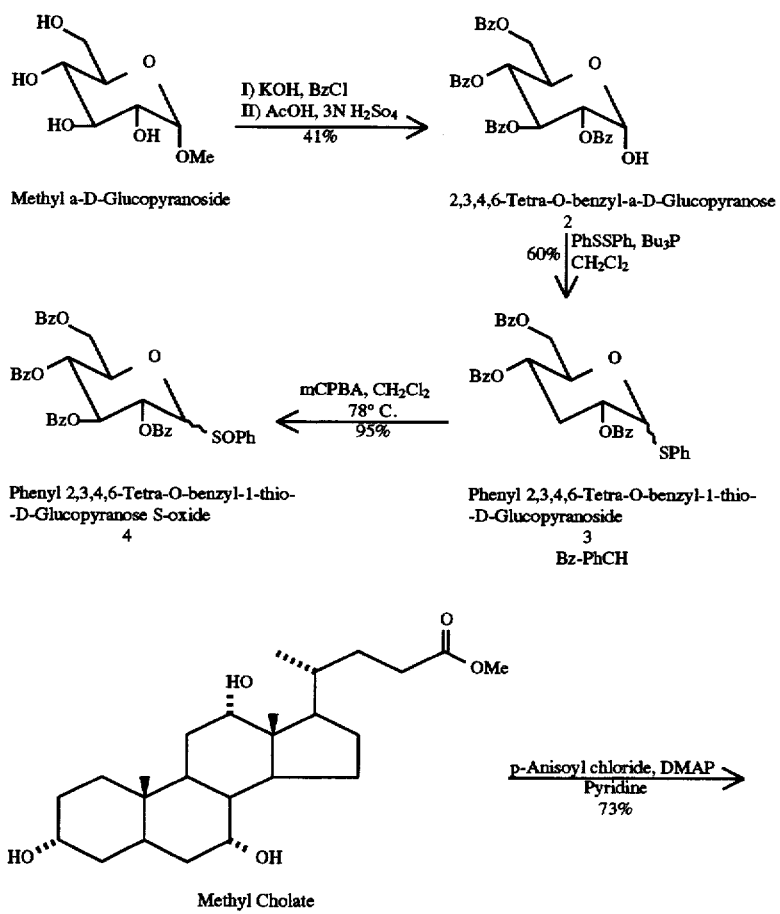

-continued
SCHEME B

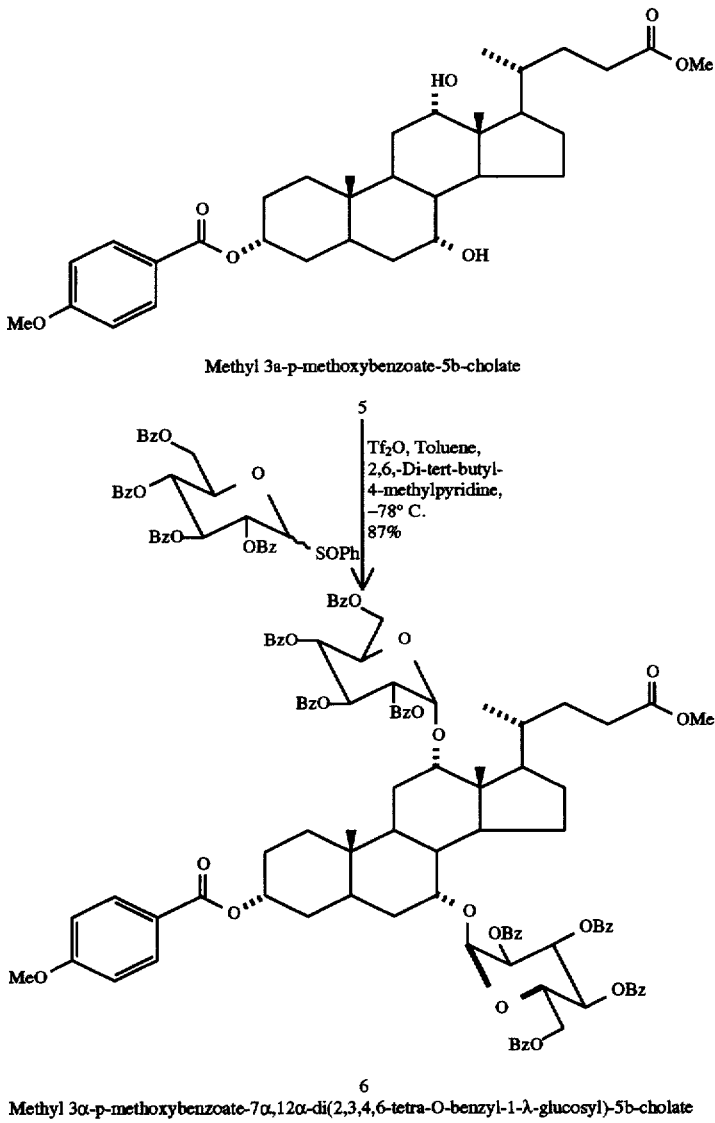

Methyl 3α-p-methoxybenzoate-7α,12α-di(2,3,4,6-tetra-O-benzyl-1-λ-glucosyl)-5b-cholate To a stirred solution of above crude compound in glacial acetic acid (700 mL) at 110° C. is added 3N sulfuric acid (120 mL) dropwise during 15 min. After 3 h the reaction mixture is cooled to room temperature and left over night for crystalization of product. The crystals are filtered, washed consecutively with water (4×500 mL) and methanol (2×250 mL), and air dried to afford 2 (115 g, 41% overall two steps) as a white powder (mp 150°–51° C., Lit. 151°–152° C.; See, Perrine, T. D. et al. *J. Org. Chem.* (1967) 32:664). TLC $R_f$=0.2 (solvent- EtOAC: Hexane=3:7). IR (KBr): 3362, 3030, 2911, 2863, 1454, 1357, 1146, 1088 cm$^{-1}$. $^1$H NMR (300 MHz, CDCl$_3$): 7.38–7.10 (m, 20H), 5.21 (d, J=3.3 Hz, 1H), 4.98–4.44 (m, 9H), 4.25 (m, 1H), 3.72–3.50 (m, 4H). Anal. Calc. for C$_{34}$H$_{36}$O$_6$: C, 75.53; H, 6.71. Found: C, 75.68; H, 6.80.

Example 4: Phenyl 2,3,4,6-tetra-O-benzyl-1-thio-D-glucopranoside (3)

To a stirred solution of 2 (108 g, 0.2 mol) and phenyl disulfide (53 g, 0.24 mol) in dichloromethane (500 mL) is added tri-n-butylphosphine (60 mL, 90%, 0.22 mol). After allowing the reaction mixture to stir at room temperature for 15 h, it is poured into a solution of saturated aqueous sodium bicarbonate (600 mL) and stirred for 10 min. The organic layer is separated, washed with water (2×500 mL), dried (Na$_2$SO$_4$) and concentrated. The oily residue is dissolved in hexane (500 mL) and chilled to 0° C. to give compound 3 (75 g, 60%) as a white solid (mp 85°–86° C. Lit. 84°–85° C. for β-thio compound; See, Ferrier, R. J. et al. Carbohyd. Res. (1973) 27:55). TLC R$_f$=0.6 (solvent—EtOAC:Hexane=1:3). IR (KBr): 3061, 3030, 2900, 2865, 1584, 1494, 1453, 1358, 1125, 1085, 1070, 1029 cm-1. $^1$H NMR (300 MHz, CDCl$_3$): 7.70–7.00 (m, 25H), 4.90–4.40 (m, 9H), 3.80–3.40 (m, 6H). Anal. Calc. for C$_{40}$H$_{40}$O$_5$S: C, 75.92; H, 6.38, S, 5.06. Found: C, 75.99; H, 6.39; S, 5.12.

Example 5: Phenyl 2,3,4,6-tetra-O-benzyl-1-thio-D-glucopranoside S-oxide (4)

To a stirred cooled (—78° C.) solution of 3 (130 g, 0.2 mol) in dichloromethane (400 mL) is added dropwise over a period of 20 min a solution of mCPBA (74%, 58.31 g, 0.25 mol) in dichloromethane (300 mL). The mixture is stirred and allowed to warm up to —30° C. The mixture is then filtered. The filtrate is washed with saturated aqueous sodium bisulfite (2×300 mL), sodium bicarbonate (2×400 mL), brine (400 mL) and water (2×400 mL). The organic layer is dried ($Na_2SO_4$) and concentrated. Flash chromatography ($CH_2Cl_2$:EtOAC=9:1) of the residue furnishes sulfoxide mixture 4 (127 g, 95%) as a white solid (mp 120°–122° C.). TLC $R_f$=0.3 (solvent—EtOH:$CH_2Cl_2$=1:9). IR (KBr): 3060, 3030, 2910, 2867, 1495, 1450, 1360, 1210, 1136, 1092, 1049 $cm^{-1}$. $^1H$ NMR ($CDCl_3$): 7.72–7.14 (m, 25H), 5.12–4.42 (m, 9H), 4.40–3.30 (m, 6H). Anal. Calc. for $C_{40}H_{40}O_6S$: C, 74.04; H, 6.22; S, 4.93. Found: C, 74.10; H, 6.26; S, 4.99.

Example 6. Methyl 3α-p-methoxybenzoate-5β-cholate (5)

A solution of methyl cholate (42.2 g, 0.1 mol), p-anisoyl chloride (20 mL, 0.133 mol) and DMAP (1 g) in pyridine (500 mL) is stirred and refluxed for 8 h. Additional p-anisoyl chloride (10 mL, 0.67 mol) is added and stirred 12 h. The reaction mixture is concentrated, and the residue is dissolved in dichloromethane (600 mL). The solution is washed consecutively with 1N HCl (2×500 mL) and water (3×500 mL), dried ($Na_2SO_4$) and the solvent allowed to evaporate. Crystallization of the residue from EtOAC/hexane (1:1) furnishes 5 (40 g, 72%) as a white solid (mp 179°–180° C.). TLC $R_f$=0.7 (solvent—EtOAC:Hexane=7:3).

Example 7: Methyl 3α-p-methoxybenzoate-7α,12α-di-(2',3',4',6'-tetra-O-benzyl (1'-α-glucosyl)-5-cholate (6)

Triflic anhydride (30 mL, 0.178 mol) is added to cooled toluene (300 mL, –78° C.) and stirred for 5 min. To this solution, a dried (by azeotropic distillation from toluene) sulfoxide 5 (97 g, 0.1495 mol) dissolved in toluene (300 mL) is added dropwise. After 15 min of stirring, a solution of dried (by azeotropic distillation with toluene) 2,6-di-ter-butyl-4-methyl-pyridine (30.8 g, 0.150 mol) in toluene (100 mL) is added to the reaction mixture and stirred for 10 min at –78° C. To this reaction mixture, dried (by azeotropic distillation with toluene) methyl cholate derivative 5 (33.36 g, 0.06 mol) in $CH_2Cl_2$ and toluene (1:1, 200 mL) is added dropwise. The reaction progress is monitored by TLC. The temperature of the reaction mixture is slowly brought to –50° C. (during 45 min) and during this time the spot of 5 on the TLC disappears completely. The reaction mixture is poured into a saturated aqueous solution of sodium bicarbonate (1000 mL) and stirred for 10 min. The organic layer is separated, and the aqueous layer is extracted with dichloromethane (2×100 mL). The combined organic layers is washed with water (3×500 mL), dried ($Na_2SO_4$) and concentrated. The residue purified by flash chromatography (EtOAC:Hexane=1:9 to 1:4) to furnish 6 (84 g, 87%) as a white foam (mp 46°–48° C.). TLC $R_f$=0.3 (solvent—EtOAC:Hexane=1:3). IR (KBr): 3084, 3062, 3028, 2936, 2867, 1735, 1707, 1605, 1496, 1453, 1360, 1321, 1275, 1254, 1210, 1165, 1097, 1073, 1030 $cm^{-1}$. $^1H$ NMR ($CDCl_3$): 7.60–6.70 (m, 43H), 5.95 (d, 1H, J=9Hz), 4.99 (d, 1H, J=3.6 Hz), 4.93 (d, 1H, 6 Hz), 4.88–3.29 (m, 31H), 2.68–0.65.(m, 37H). Fab MS: 1624 (M+Na)⁺. Anal. Calc. for $C_{101}H_{116}O_{17}$: C, 75.71; H, 7.30. Found, C, 75.59; H, 7.31.

Example 8: 7α,12α-Di-(2',3',4',6'-tetra-O-benzyl-1'α-glucosyl)-5β-cholan-24-oic acid (7)

To a stirred solution of 6 (24 g, 15 mmol) in THF (150 mL), NaOH (10 g, 250 mmol) in 95% Ethanol (200 mL) is added and refluxed for 48 h, as shown in Scheme C. The reaction mixture is then concentrated, and the residue is dissolved in ethyl acetate (300 mL), washed with water (2×250 mL), saturated aqueous sodium bicarbonate (2×300 mL), brine (300 mL) and dried ($Na_2SO_4$). Solvent is evaporated and the resulting compound 7 (18.5 g, 85%) is used for the next step without further purification. TLC $R_f$=0.4 (solvent—EtOAC:Hexane=1:3) 0.4.

SCHEME C

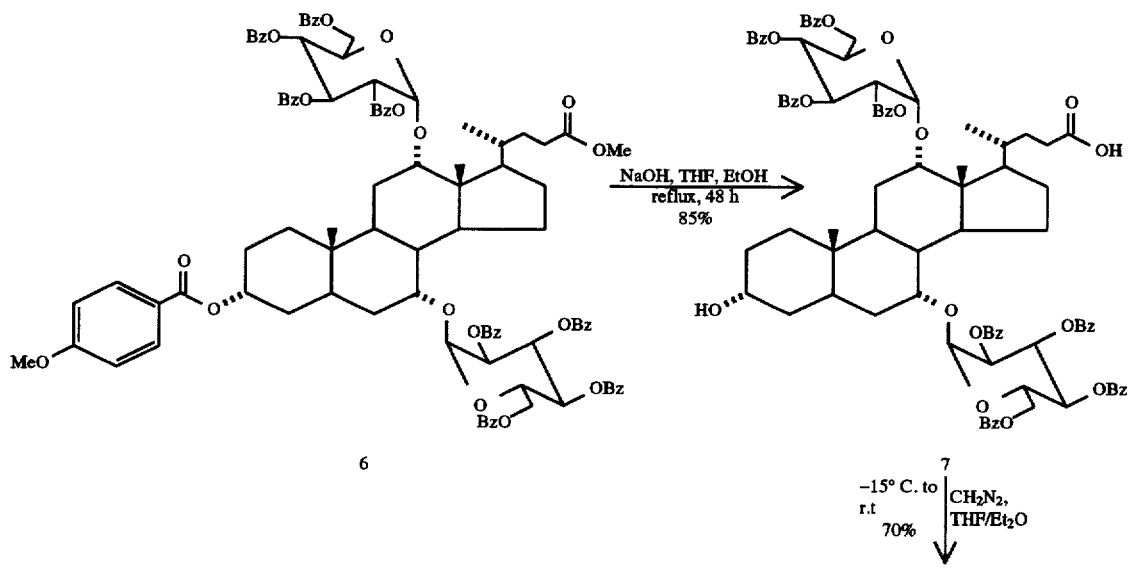

SCHEME C -continued

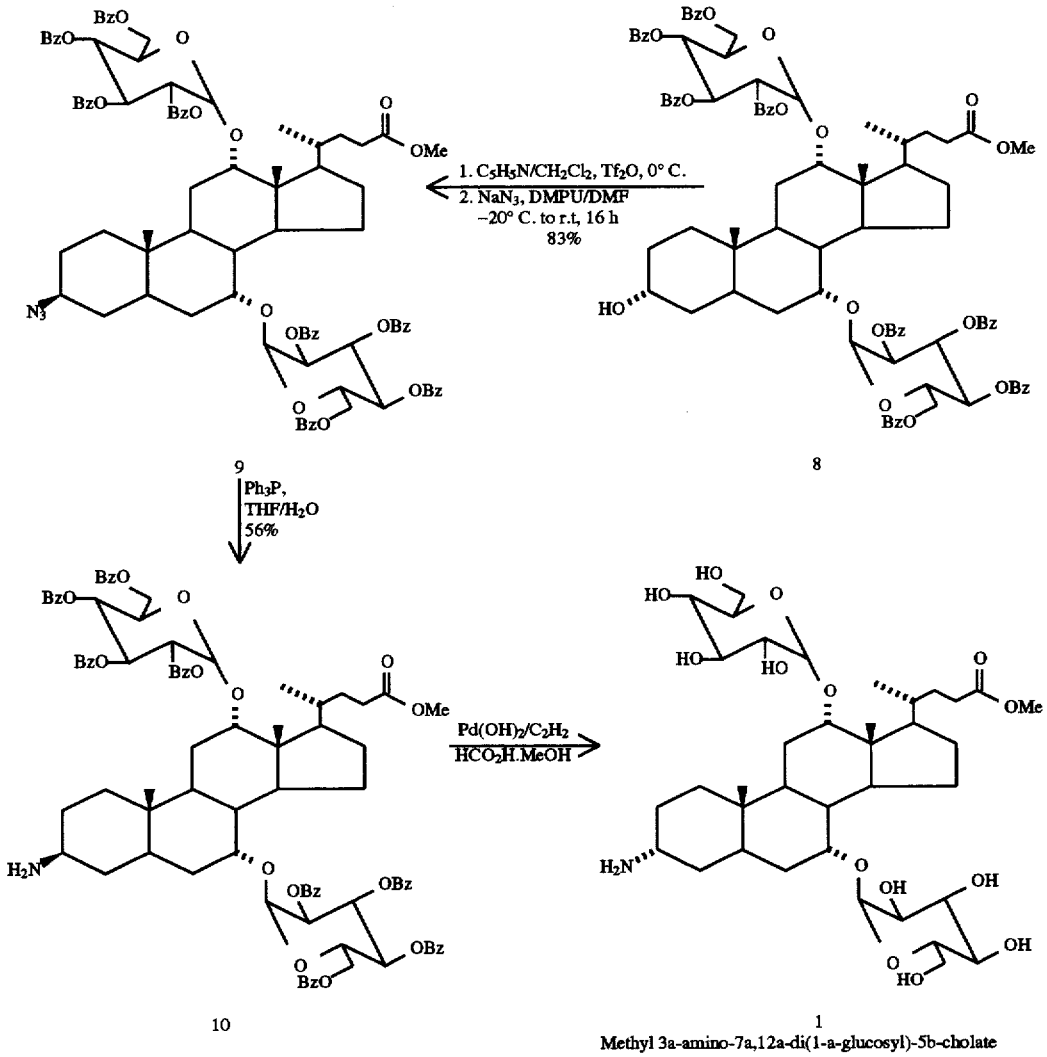

10

1
Methyl 3a-amino-7a,12a-di(1-a-glucosyl)-5b-cholate

Example 9: Methyl 7α,12α-di-(2',3',4',6'-tetra-O-benzyl-1'α-glucosyl)-5β-cholate (8).

A cooled (−10° C.) solution of diazomethane in ether (100 mL, generated from 5.35 g of diazalid, 25 mmol) is added to a cooled (−10° C.) solution of 7 (18.5 g, 12.74 mmol) in ether (100 mL). After 1 h, excess diazomethane is destroyed by adding glacial acetic acid (2 mL). The reaction mixture is washed consecutively with saturated aqueous sodium bicarbonate (2×400 mL), brine (300 mL), and water (300 mL), dried ($Na_2SO_4$), and concentrated. The residue is purified by flash chromatography (EtOAC:Hexane=3:17) to furnish 8 (13 g, 70%) as a gum. TLC $R_f$=0.6 (solvent—EtOAC:Hexane=1:3). IR (Neat): 3450, 2925, 2866, 1736, 1453, 1362, 1158, 1071, 1030 cm$^{-1}$. $^1$H NMR (CDCl$_3$): 7.40–6.50 (m, 40H), 5.10–3.40 (m, 33H), 2.40–0.71 (m, 38H). Anal. Calc. for $C_{93}H_{110}O_5$: C, 76.08; H, 7.56. Found: C, 74.79; H, 7.50.

Example 10: Methyl 3β-azido-7α,12α-di-(2',3',4',6'-tetra-O-benzyl-1'α-glucosyl)-5β-cholate (9)

To a cooled (0° C.) solution of methyl cholate derivative 8 (13 g, 8.87 mmol) and pyridine (2.5 mL, 31 mmol) in dichloromethane (50 mL), triflic anhydride is added and allowed to stir for 20 min. To this mixture, a solution of sodium azide (2.6 g, 40 mmol) in DMF/DMPU (1:1, 250 mL) is then added at −20° C. The reaction mixture is allowed to warm up to room temperature, where it is stirred overnight. The solvents are evaporated, and the residue is dissolved in dichloromethane (200 mL), washed with water (3×200 mL), dried ($Na_2SO_4$), and concentrated. Flash Chromatography of the residue on silica (EtOAC:Hexane=3:17) furnishes 10 g (75%) of 9 as a white solid (top 112°–114° C.). TLC $R_f$=0.6 (solvent—EtOAC:Hexane=1:4). IR (KBr): 3085, 3061, 3029, 2921, 2867, 2097, 1735, 1603, 1495, 1452, 1360, 1256, 1207, 1160, 1091, 1071, 1031 cm$^{-1}$. $^1$H NMR (CDCl$_3$): 7.37–6.84 (m, 40H), 5.15 (d, 1H, J=4Hz), 4.95 (d, 1H, 4Hz), 4.86–4.26 (m, 15H), 4.08–3.40 (m, 16H), 2.60–0.71 (m, 37H). Fab MS: 1515 (M+Na)$^+$. Anal. Calc. for $C_{93}H_{110}O_{14}N_3$: C, 74.76; H, 7.43; N, 2.81. Found: C, 74.84; H, 7.40; N, 2.79.

Example 11: Methyl 3β-amino-7α,12α-di-(2',3',4',6'-tetra-O-benzyl-1'α-glucosyl)-5β-cholate(10)

A solution of compound 9 (11 g, 7.38 mmol) and Ph$_3$P (5.76 g, 22 mmol) in 90% aqueous THF (100 mL) is stirred and refluxed for 48 h. The reaction mixture is concentrated, and the residue is purified by flash chromatograph (CH$_2$Cl$_2$ and then $CH_2Cl_2$: EtOH=98:2 to 9:1) to give the 3-amino compound 10 (6 g, 56%) as a white solid (top 43°–45° C.). TLC $R_f$=0.15 (solvent—EtOH:$CH_2Cl_2$=1:19. IR (KBr): 3418, 2922, 2868, 1736, 1496, 1453, 1362, 1161, 1071, 1032 cm$^{-1}$. $^1$H NMR (CDCl$_3$): 7.38–6.84 (m, 40H), 5.10–3.48 (m, 33H), 2.62–0.70 (m, 37H). Anal. Calc. for $C_{93}H_{112}O_{14}N$: C, 76.08; H, 7.70; N, 0.95. Found: C, 75.82; H, 7.71; N, 0.89.

Example 12: Methyl 3β-amino-7α,12α-di-(1'-α-glucosyl)-5β-cholate (1)

To a solution of 10 (14.65 g, 10 mmol) in toluene (50 and ethanol (200 mL) is added formic acid (15 mL) and palladium hydroxide (20%) on carbon (15 g). The resulting mixture is stirred for 24 h under a hydrogen atmosphere at 40 psi. TLC indicated incomplete hydrogenolysis. Additional formic acid (4 mL) and catalyst (4 g) is then added, and the hydrogenation reaction allowed to proceed for another 24 h. The reaction mixture is then filtered through sand over a membrane filter and concentrated. The filtrate is then mixed with ethyl acetate to form a precipitate. (Some of the methanol solvent from the hydrogenation reaction may need to be removed.) The filtered precipitate is then dissolved in 25 mL deionized water and freezedried. Flash Chromatography gives 2.82 g (38%) of 1 as white foam (mp 170°–172° C., decomp.). TLC $R_f$=0.15 (solvent—MeOH:$CH_2Cl_2$:Isopropylamine=2:2:1). IR (KBr): 3450, 2932, 1736, 1595, 1451, 1381, 1151, 1023 cm-1. $^1$HNMR (CDCl$_3$): 5.05 (d, 1H), 4.80 (d, 1H), 3.91–3.10 (m, 15H), 2.50–0.58 (m, 37H). MS (Fab): 746 (M+H)$^+$. Anal. Calc. for $C_{36}H_{63}O_{14}N$: C, 59.56; H, 8.52; N, 1.88. Found: C, 54.60; H, 8.47; N, 2.49.

Example 13: Methyl 3-p-methoxybenzoate-7α,12α-di-(1'-α-glucosyl)-5β-cholate (Entry No. 8$^h$, Table I, Below)

To a solution of 6 (10 mmol; See, Example 7, above) in toluene (50 mL) and ethanol (200 mL) is added formic acid (15 mL) and palladium hydroxide (20%) on carbon (15 g). The resulting mixture is stirred for 24 h under a hydrogen atmosphere at 40 psi. (Additional formic acid and catalyst can be added, if desired, if TLC analysis reveals that the reaction is incomplete after the initial 24 h reaction period. A second 24 h reaction period can then be initiated.) The reaction mixture is then filtered through sand over a membrane filter and concentrated. The filtrate is then mixed with ethyl acetate to form a precipitate. (Some of the methanol solvent from the hydrogenation reaction may need to be removed.) The filtered precipitate is then dissolved in 25 mL deionized water and freeze-dried. Subjecting the residue to flash column chromatography gives the title compound in ca. 38% yield.

$^1$HNMR (CD$_3$OD): δ0.71 (s, 3H, 18-H), 0.90 (d,J=6.6Hz; 3H, 21-H), 0.93 (s, 3H, 19-H), 1.0–2.6(m), 3.2–3.4 (m, 2H), 3.55 (s, 3H, CO$_2$CH$_3$), 365(m), 376(s, 3H, anisoyl-4-methyl), 4.83 (d, 1H, anomeric), 5.02 (d, 1H, anomeric), 6.87 (d, J=9Hz, 2H, anisoyl aromatic), 7.92 (d,J=9Hz, 2H, anisoyl aromatic).

Additional compounds that can be prepared following procedures analogous to those outlined above are shown in Table I, including selected mass spectral and proton nmr data.

TABLE I

| Entry No. | A | a* | R$^{1*}$ | R$^2$ | R$^{3**}$ | R$^{4**}$ | R$^5$ | n |
|---|---|---|---|---|---|---|---|---|
| 1$^b$ | O‖OCOEt | s(α) | H(β) | CH$_3$ | O-glucose(α) | O-glucose(α) | CO$_2$Me | 2 |
| 2$^c$ | OCOPh | s(α) | H(β) | CH$_3$ | O-glucose(β) | O-glucose(β) | CO$_2$Me | 2 |
| 3$^d$ | OH | s(α) | H(β) | CH$_3$ | O-glucose(α) | O-glucose(α) | CO$_2$H | 2 |
| 4* | OH | s(α) | H(β) | CH$_3$ | O-glucose(α) | O-glucose(α) | CO$_2$Me | 2 |
| 5$^f$ | OH | s(α) | H(β) | CH$_3$ | O-glucose(α) | O-glucose(α) | CONH-Tryptophan | 2 |
| 6 | O‖OCOEt | s(α) | H(α) | CH$_3$ | O-glucose(α) | O-glucose(α) | CO$_2$Me | 2 |
| 7$^g$ | OCOPh | s(α) | H(β) | CH$_3$ | O-glucose(α) | O-glucose(α) | CO$_2$Me | 2 |
| 8$^h$ | OCOPh—OMe | s(α) | H(β) | CH$_3$ | O-glucose(α) | O-glucose(α) | CO$_2$Me | 2 |
| 9$^i$ | OCOPh | s(α) | H(α) | CH$_3$ | O-glucose(β) | O-glucose(β) | CO$_2$Me | 2 |
| 10$^j$ | OH | s(α) | H(β) | CH$_3$ | O-glucose(β) | O-glucose(β) | CO$_2$H | 2 |
| 11$^k$ | OCOPh | s(α) | H(α) | CH$_3$ | O-glucose(α) | O-glucose(α) | CO$_2$Me | 2 |
| 12 | OH | s(α) | H(α) | CH$_3$ | O-glucose(α) | O-glucose(α) | CO$_2$H | 2 |
| 13$^l$ | OH | s(α) | H(α) | CH$_3$ | O-glucose(β) | O-glucose(β) | CO$_2$H | 2 |
| 14 | NH$_2$ | s(α) | H(β) | CH$_3$ | O-glucose(α) | O-glucose(α) | CO$_2$H | 2 |

TABLE I-continued

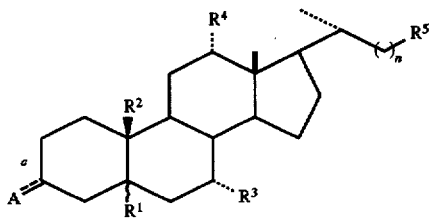

| Entry No. | A | a* | R¹* | R² | R³ | R⁴ | R⁵ | n |
|---|---|---|---|---|---|---|---|---|
| 15 | O=COEt (OCOEt) | s(α) | H(β) | CH₃ | O-glucose(β) | O-glucose(β) | CO₂Me | 2 |
| 16 | O=COEt (OCOEt) | S(α) | H(α) | CH₃ | O-glucose(β) | O-glucose(β) | CO₂Me | 2 |
| 17 | O | d | H(α) | CH₃ | O-glucose(α) | O-glucose(α) | CO₂H | 2 |
| 18 | O | d | H(α) | CH₃ | O-glucose(β) | O-glucose(β) | CO₂H | 2 |
| 19 | O | d | H(β) | CH₃ | O-glucose(α) | O-glucose(α) | CO₂H | 2 |
| 20 | O | d | H(β) | CH₃ | O-glucose(β) | O-glucseo(β) | CO₂H | 2 |
| 21 | O | d | H(α) | CH₃ | O-glucose(α) | O-glucose(α) | CO₂Me | 2 |
| 22 | O | d | H(α) | CH₃ | O-glucose(β) | O-glucose(β) | CO₂Me | 2 |
| 23 | O | d | H(β) | CH₃ | O-glucose(α) | O-glucose(α) | CO₂Me | 2 |
| 24 | O | d | H(β) | CH₃ | O-glucose(β) | O-glucose(β) | CO₂Me | 2 |
| 25 | OCH₂Ph | s(α) | H(α) | CH₃ | O-glucose(α) | O-glucose(α) | CO₂H | 2 |
| 26 | OCH₂Ph | s(α) | H(α) | CH₃ | O-glucose(β) | O-glucose(β) | CO₂H | 2 |
| 27 | OCH₂Ph | s(α) | H(β) | CH₃ | O-glucose(α) | O-glucose(α) | CO₂H | 2 |
| 28 | OCH₂Ph | s(α) | H(β) | CH₃ | O-glucose(β) | O-glucose(β) | CO₂H | 2 |
| 29 | OCH₂Ph | s(α) | H(α) | CH₃ | O-glucose(α) | O-glucose(α) | CO2Me | 2 |
| 30 | OCH₂Ph | s(α) | H(α) | CH₃ | O-glucose(β) | O-glucose(β) | CO₂Me | 2 |
| 31 | OCH₂Ph | s(α) | H(β) | CH₃ | O-glucose(α) | O-glucose(α) | CO₂Me | 2 |
| 32 | OCH₂Ph | s(α) | H(β) | CH₃ | O-glucose(β) | O-glucose(β) | CO₂Me | 2 |
| 33 | O=COEt (OCOEt) | s(α) | H(α) | CH₃ | O-galactose(α) | O-galactose(α) | CO₂H | 2 |
| 34 | O=COEt (OCOEt) | s(α) | H(α) | CH₃ | O-galactose(β) | O-galactose(β) | CO₂H | 2 |
| 35 | O=COEt (OCOEt) | s(α) | H(β) | CH₃ | O-galactose(α) | O-galactose(α) | CO₂H | 2 |
| 36 | O=COEt (OCOEt) | s(α) | H(β) | CH₃ | O-galactose(β) | O-galactose(β) | CO₂H | 2 |
| 37 | O=COEt (OCOEt) | s(α) | H(α) | CH₃ | O-galactose(α) | O-galactose(α) | CO₂Me | 2 |
| 38 | O=COEt (OCOEt) | s(α) | H(α) | CH₃ | O-galactose(β) | O-galactose(β) | CO₂Me | 2 |
| 39 | O=COEt (OCOEt) | s(α) | H(β) | CH₃ | O-galactose(α) | O-galactose(α) | CO₂Me | 2 |
| 40 | O=COEt (OCOEt) | s(α) | H(β) | CH₃ | O-galactose(β) | O-galactose(β) | CO₂Me | 2 |
| 41 | OCOPh | s(α) | H(α) | CH₃ | O-ribose(α) | O-ribose(α) | CO₂H | 2 |
| 42 | OCOPh | s(α) | H(α) | CH₃ | O-ribose(β) | O-ribose(β) | CO₂H | 2 |
| 43 | OCOPh | s(α) | H(β) | CH₃ | O-ribose(α) | O-ribose(α) | CO₂H | 2 |
| 44 | OCOPh | s(α) | H(β) | CH₃ | O-ribose(β) | O-ribose(β) | CO₂H | 2 |
| 45 | OCOPh | s(α) | H(α) | CH₃ | O-ribose(α) | O-ribose(α) | CO₂Me | 2 |
| 46 | OCOPh | s(α) | H(α) | CH₃ | O-ribose(β) | O-ribose(β) | CO₂Me | 2 |
| 47 | OCOPh | s(α) | H(β) | CH₃ | O-ribose(α) | O-ribose(α) | CO₂Me | 2 |
| 48 | OCOPh | s(α) | H(β) | CH₃ | O-ribose(β) | O-ribose(β) | CO₂Me | 2 |

TABLE I-continued

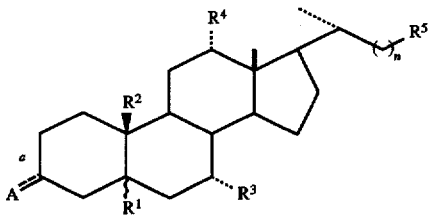

| Entry No. | A | a* | R¹* | R² | R³ | R⁴ | R⁵ | n |
|---|---|---|---|---|---|---|---|---|
| 49 | O‖OCOEt | s(α) | H(β) | $CH_3$ | O-glucose(α) | O-glucose(β) | $CO_2Me$ | 2 |
| 50 | O‖OCOEt | s(α) | H(β) | $CH_3$ | O-glucose(β) | O-glucose(α) | $CO_2Me$ | 2 |
| 51 | O‖OCOEt | s(α) | H(α) | $CH_3$ | O-glucose(α) | O-glucose(β) | $CO_2Me$ | 2 |
| 52 | O‖OCOEt | s(α) | H(α) | $CH_3$ | O-glucose(β) | O-glucose(α) | $CO_2Me$ | 2 |

*s = single bond
d = double bond
α = below the plane of the ring
β = above the plane of the ring

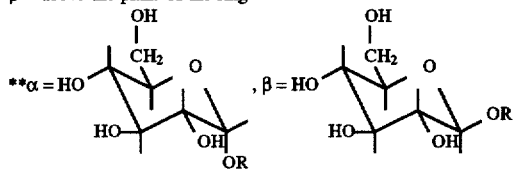

An α-glucoside    A β glucoside

Mass Spectra
c  m/e = 851
d  m/e = 771
h  m/e = 881
i  m/e = 851
j  m/e = 771
k  m/e = 851
l  m/e = 771

¹H NMR
b: ($CDCl_3$, 500MH$_z$) δ: 5.04(m, 1H, anomeric β-H), 4.82(m, 1H, anomeric β-H)
e: ($CDCl_3$, 500MH$_z$) δ: 5.04(m, 1H, anomeric β-H), 4.82(m, 1H, anomeric β-H)
f: ($CDCl_3$, 500MH$_z$) δ: 5.056(m, 1H, anomeric β-H), 5.0414(m, 1H, anomeric β-H)
g: ($CDCl_3$, 500MH$_z$) δ: 5.0525(d, J=3.96H$_z$, 1H, anomeric β-H), 4.860(d, J=3.96Hz, 1H, anomeric β-H)

Example 14. Synthesis of the Activated Ester of Deoxycholate

Triethylamine (10 mL, 71.2 mmol) is added to a stirred solution of the sodium salt of deoxychoic acid (15 g, 34.7 mmol), N-hydroxysuccinimide (7.5 g, 65.2 mmol), 1-hydroxybenzotriazole hydrate (9.3 g, 68.8 mmol, HOBT) and 1-(3-dimethylaminopropyl)-3-ethylcarbodiimide (13.2 g, 69.3 mmol, EDC) in dichloromethane. The mixture is stirred for 12 h. The reaction mixture is then diluted with water (150 mL) and extracted twice with dichloromethane. The organic layers are combined, dried over $MgSO_4$, filtered, and concentrated under reduced pressure to provide a solid residue. The residue is recrystallized from ethyl acetate-petroleum ether to give 5.5 g (30%) of product. Selected ¹H resonances: (270 MHz, $CDCl_3$) 4.00 ppm, 1H, C12, bs; 3.6 ppm, 1H, C3, m; 1.03. ppm, 3H, C17, d; 0.9 ppm and 0.68, 3H each, angular methyls of steroid, s.

Example 15. Synthesis of the Deoxycholatespermine Conjugate

Spermins (0.3 g, 1.18 mmol) is added to a stirred solution of the activated ester of deoxycholate (0.15 g, 0.28 mmol) and triethylsmine (0.1 mL, 0.71 mmol) in dichloromethane. The mixture is stirred for 0.5 h and a precipitate is observed. The solids are filtered through a buchner funnel. The filtrate is washed with water (10 mL). The organic layer is concentrated to give a residue (0.18 g). The residue is acidified with methanolic trifluoroacetic acid. The resulting solution is purified by reverse phase chromatography to give 0.14 g (80%) of the steroid-polyamine conjugate. Selected ¹H resonances: (270 MHz, $CD_3OD$) 3.98 ppm, 1H, C12, bs; 3.55 ppm, 1H, C3, m; 3.4 ppm, 2H, spermine methylenes next to amide linkage, bt; 3.0 ppm, 10H spermine methylenes except those next to amide, bs; 1.03 ppm, 3H, C17, d; 0.9 ppm and 0.68, 3H each, angular methyls of steroid, s. High resolution mass spectrometry has confirmed the proper molecular weight.

In the same fashion, other non-glycosylated amphiphatic steroidal compounds, including but not limited to cholic acid or chenodeoxycholic acid, may be conjugated to a polyamine molecule, including but not limited to ethylene diamine, diethylene triamine, spermine, spermidine, other polyalkylene-polyamines, and the like.

Example 16. Coupling of Leu-enkephalin to the deoxycholate-spermine conjugate

To a solution of steroid-spermine conjugate (13 mg, 0.02 mmole) is added $Na_2CO_3$ (11 mg, 0.10 mmol). The mixture is stirred for 1 h. The solids are then filtered through a buchner funnel and concentrated under reduced pressure. This residue is dissolved in 10 mL of DMF. Diisopropylethyl amine (12 µL, 0.067 mmol, DIEA), 1-hydroxybenzotriazole hydrate (9 mg, 0.067 mmol), O-benzotriazol-1-yl-tetramethyluronium hexafluorophosphate (27 mg, 0.067 mmol, HBTU) and Leu-enkephalin (10 mg, 0.015 mmol)- are added to the solution. The resulting mixture is stirred for three days.

The solvent is then removed under reduced pressure to give a residue. The residue is taken up in dichloromethane and triturated until a solid precipitated. The precipitate is purified by reverse phase chromatography to give 10 mg of a steroid peptide conjugate. Selected $^1$HNMR resonances: (270 MHz, $CD_3OD$) 7.2 ppm, 5H, Phe aromatics, m; 6.95 ppm, 2H, Tyr aromatics 2 and 6, d; 6.65 ppm, 2H, Tyr aromatics 3 and 5, d; 0.9 ppm, 3H, C17 methyl of steroid, d. High resolution mass spectrometry has confirmed the proper molecular weight.

Example 17. 3α-Hydroxy-7,12-di-(1'-α-glucosyl)-5β-cholic acid (Entry No. $3^d$, Table I, above)

To a stirred solution of the methylcholate product of Example 13, 1bove, (15 mmol) in THF (150 mL) is added NaOH (10 g, 250 mmol) in 95% ethanol (200 mL). The reaction mixture is refluxed for 48 h. The reaction mixture is then concentrated, and the residue is dissolved in ethyl acetate (300 mL), washed with water (2×250 mL), saturated aqueous sodium bicarbonate (2×300 mL), brine (300 mL) and dried ($Na_2SO_4$). Solvent is evaporated to provide the glycosteroid acid product in 80% yield. Activation of the carboxylic acid group is carried out as follows.

Example 18. Synthesis of the glycosteroidspermine conjugate via the activated acid Triethylamine (120 µL, 0.8 mmol) is added to a stirred solution of the glycosteroid acid (0.3 g, 0.2 mmol; See, above), N-hydroxysuccinimide (72 mg, 0.6 mmol), 1-hydroxybenzotriazole hydrate (112 mg, 0.8 mmol) and 1-(3-dimethylaminopropyl)-3-ethylcarbodiimide (160 mg, 0.8 mmol) in dichloromethane. The mixture is stirred for 12 h. After this time, the reaction mixture is diluted with water (50 mL) and extracted twice with dichloromethane. The organic layers are combined, dried over $MgSO_4$, filtered, and concentrated under reduced pressure to provide a solid residue 0.33 g (96%) of the activated ester.

To a stirred solution of the activated ester (0.15 g, 0.089 mmol) and triethylamine (50 mL, 0.35 mmol) in dichloromethane is added spermine (0.3 g, 0.61 mmol). The mixture is stirred for 0.5 h and a precipitate is observed. The solids are filtered over a buchner funnel. The filtrate is washed with water (10 mL). The organic layer is concentrated to give a residue (0.18 g). The residue is acidified with methanolic trifluoroacetic acid. The resulting solution is purified by reverse phase chromatography to give 0.14 g (85%) of the glycosteroid-polyamine conjugate.

In the same fashion, other glycosylated amphiphatic steroidal compounds, including but not limited to the mono-, di-, or triglycosylated forms (as appropriate) of cholic acid, 7-deoxycholic acid, or chenodeoxycholic acid, may be conjugated to a polyamine molecule, including but not limited to ethylene diamine, diethylene triamine, spermine, spermidine, other polyalkylenepolyamines, and the like.

Example 19. Deprotection of the protected glycosteroid-polyamineconjugate

A hydrogenation flask is charged with a solution of the protected glycosteroid-spermine conjugate (0.11 g, 0.06 mmol; See, above) in a mixture of methanol (20 mL) and benzene (4 mL), followed by $Pd(OH)_2$ catalyst and formic acid (1 mL). The reaction mixture is shaken under a hydrogen atmosphere at 50 psi for 40 h. The catalyst is filtered off with Celite, and the solvent is removed by evaporation under reduced pressure. The product is purified over Sephadex-LH-20 gel, eluting with MeOH, to give the desired glycosteroid-spermine conjugate.

Example 20. Leu-enkephalin conjugate of the deprotected glycosteroid with the spermine polyamine "linker"

Triethylamine (0.8 mmol) is added to a stirred solution of tert-butylcarbonyl (Boc)-protected Leu-enkephalin (0.2 mmol), N-hydroxysuccinimide (0.6 mmol), 1-hydroxybenzotriazole hydrate (0.8 mmol) and 1-(3-dimethylaminopropyl)-3-ethylcarbodiimide (0.8 mmol) in dichloromethane. The mixture is stirred for 12 h. After this time, the reaction mixture is diluted with water (50 mL) and extracted twice with dichloromethane. The organic layers are combined, dried over $MgSO_4$, filtered, and concentrated under reduced pressure to provide the activated Boc-Leu-enkephalin in good yield.

To a stirred solution of the activated Boc-Leu-enkephalin (0.089 mmol) and triethylamine (0.35 mmol) in dichloromethane is added the deprotected glycosternidspermine conjugate described above (0.61 mmol). The mixture is stirred for 0.5 h and a precipitate is observed. The solids are filtered over a buchner funnel. The filterate is washed with water (10 mL). The organic layer is concentrated to give a residue, which is acidified with methanolic trifluoroacetic acid. The resulting solution is purified by reverse phase chromatography to give the desired Boc-Leu-enkephalin conjugate in good yield.

USE

The compounds of the invention have been shown to interact with, and permeabilize, biological membranes and to enhance the efficacy of antibiotics and antifungal agents in living cells. Since the compounds of the invention have been shown to permeabilize membranes, and the compounds themselves have no effect on cell growth at the concentrations used, it is presumed that the enhanced efficacy is related to increased delivery of the therapeutically-significant-compounds to the cells.

The utility of the compounds for permeabilizing membranes was demonstrated using an assay (Hoyt, D. W., et al. Biochemistry (1991) 30:10155) in which a fluorescein derivative is encapsulated at self-quenching concentrations inside vesicles. An increase in fluorescent intensity upon addition of a test compound indicates leakage of the fluorescein derivative out of the vesicle and therefore implies a disruption or perturbation of the membrane. The compounds of the present invention induced a rapid and significant increase in fluorescen intensity at very low concentrations (0.05 mM–0.5 mM), indicating phospholipid membrane permeabilization.

In addition, both light scattering and turbidity measurements on vesicles treated with selected glycosylated steroid derivatives (at concentrations which induce 100% leakage of carboxyfluorescein) showed that the average size of the vesicles was not significantly different from that of untreated vesicles. Moreover, electron micrographs of vesicles treated with selected glycosylated steroid derivatives (at concentrations which induce 100% leakage of carboxyfluorescein) did not show significant changes in morphology relative to untreated vesicles. The glycosylated steroid derivatives of the present invention, therefore, permeabilize membranes without destroying the vesicles or inducing extensive fusion.

The inventors believe, based on NMR studies of aggregates in solution and also on crystallographic evidence, that the glycosylated steroids of the present invention self-associate and insert into membranes in an associated form, and that membrane permeabilization is related to this process. Although the pure phospholipid vesicles used in this assay do not have the complexity of biological membranes, the inventors have shown that compounds which work well in this assay also enhance the action of therapeutically-significant-compounds (e.g., antibacterial agents and antifungal agents) on living cells. This finding supports the proposition that the ability of the glycosylated steroid derivatives to interact with phospholipid bilayers is related to the ability of the derivatives to enhance the therapeutic efficacy of therapeutically-significant-compounds. It further indicates that the carboxyfluorescein assay is a reasonable initial model system for identifying potential candidates for the permeabilization of biological membranes.

A variation of the above-mentioned assay (Carmichael, V E et al. *J. Am. Chem. Soc.* (1989) Vol. 111(2):767–769) was employed to determine whether the compounds make the membranes permeable to protons at extremely low concentrations (0.01 mM–0.005 mM). For this assay, the fluorescein derivative was encapsulated inside vesicles at non-quenching concentrations in a solution of pH 6.5. The vesicles were then diluted into a second solution buffered at a lower pH of 5.5. A compound of Formula (I) was then added at a concentration lower than the concentration required to make the membranes permeable to the fluorescein derivative. After addition of compounds of the Formula (I), the fluorescent intensity within the vesicles decreased, indicating a lower pH resulting from the infiltration of protons from the bulk solution through the vesicles (i.e., the compounds of the present invention resulted in the permeabilization of the vesicles at very low concentrations).

The utility of the glycosylated steroid derivatives of the invention for permeabilizing phospholipid membranes suggested the usefulness of the derivatives for enhancing the permeability of cell membranes, which are composed in large part of phospholipids and other lipids, to therapeutically-significant-molecules. This use was demonstrated in assays testing the efficacy of two different antifungal agents for killing *Crithidia fasciculate*. The use further was demonstrated in assays testing the efficacy of erythromycin for killing *E. coli* ATCC 25922 cells.

ASSAY I: Leakage of Carboxyfluorescein from Vesicles

To a 25 mL round bottom flask 20.5 mg egg yolk (Sigma, average MW 770.4) dissolved in CHCl$_3$/MeOH, 5.0 mg phosphatidyl glycerol (Sigma, MW 772) dissolved in CHCl$_3$/MeOH, and 12.7 mg repurified cholesterol (Aldrich, MW 386.66) were added. The molar ratio of egg yolk; phosphatidyl glycerol:cholesterol was 4:1:5 (66 moles total lipid). The solvent was removed on a rotary evaporator. The dried lipid mixture was then put under argon and 3 mL freshly distilled diethyl ether was added. After the lipid had redissolved, 1 mL of carboxyfluorescein dissolved in water (pH adjusted to 7.4) was added to a concentration of 180 mM (the concentration of carboxyfluorescein was determined by UV; the extinction coefficient at pH 7.4 is 5.6×10$^4$; $\lambda_{max}$=492). The lipid mixture containing carboxyfluorescein was sonicated under argon in a bath type sonicator at 5°–15° C. for 15–30 minutes. The mixture was then placed on the rotary evaporator and the organic solvent was removed. To separate the carboxyfluoresceinloaded vesicles from unencapsulated carboxyfluorescein, the remaining aqueous vesicle mixture was loaded on a Sephadex G-25 column equilibrated with 145 mM NaCl/10 mM Hepes at pH 7.4. The carboxyfluorescein-loaded vesicles eluted in the first fraction after the void volume while the unencapsulated carboxyfluorescein remained on the column. The purified vesicles were diluted with 145 mM NaCl/10 mM Hepes buffer (pH 7.4) until the fluorescent intensity of the vesicle mixture measured approximately 10.

Because the carboxyfluorescein is encapsulated at self-quenching concentrations in the vesicles, an increase in fluorescent intensity over time indicates that the fluorophore is leaking out of the vesicles into the buffer. 5% Triton-X 100 was added in 50 μL MeOH to a sample of the vesicle solution to determine the maximum possible fluorescent increase (Triton-X 100 is a nonionic detergent that at the high concentration used breaks vesicles by solubilizing the lipids). The ability of each glycosylated steroid to induce the release of carboxyfluorescein from the vesicles was determined by monitoring the increase in fluorescent intensity upon addition of glycosteroid. For each experiment, 50 μL of glycosteroid in methanol (initial concentrations ranged from 0.6145 to 2.458 mM) was added to the cuvette and the fluorescent intensity followed over 10 minutes. A control in which 50 μL pure methanol was added showed that methanol alone does not cause a significant increase in fluorescent intensity. However, several of the glycosteroids efficiently permeabilized vesicle membranes at very low concentrations, permitting the carboxyfluorescein to leak out into the buffer. The results are summarized in Table II.

If the concentrations required to induce significant (i.e., >50%) leakage are taken as a measure of efficacy, then compounds 7, 8, and 11, are the most effective glycosylated steroids tested for permeabilizing phospholipid membranes in this assay. (The numbers of the compounds listed in Table II and III correspond to the compound entries of Table I. For example, compound 8 of Table II corresponds to Entry 8 of Table I.) Compounds 7 and 8 have a cis A/B ring junction and two α-linked glucose sugars attached to the hydrophilic face of the molecule. Compound 11 also has two linked glucose sugars attached to the hydrophilic face of the molecule. Cholic acid, deoxycholic acid, and chenodeoxycholic acid, compounds known to permeabilize biological membranes in other uses (Gordon GS et al. Proc. Nat'l. Acad. Sci. USA (1985) 82:7419–7423) also permeabilize membranes in this assay, although at much higher concentrations than many of the compounds of the present invention. From these observations, it may be concluded that glycosylation changes the chemical properties of the steroids, making them more efficient at permeabilizing membranes.

TABLE II

| EX | CONCENTRATION (mM)* | % increase in Fluorescence |
|---|---|---|
| Cholic Acid | 0.117 | 0 |
|  | 2.341 | 59.1 |
| Methyl Cholate | 0.117 | 25.4 |
| Chenodeoxycholic | 0.117 | 17.7 |

TABLE II-continued

| EX | CONCENTRATION (mM)* | % increase in Fluorescence |
|---|---|---|
| acid | 1.17 | 80.9 |
| Triton-X 100 | 4.04 | 100 |
|  | 1.17 | 46.4 |
|  | 0.117 | 18.6 |
| Deoxycholic Acid | 0.117 | 0 |
|  | 1.17 | 82.7 |
| 1 | 0.117 | 0 |
| 2 | 0.117 | 10 |
| 3 | 2.34 | 0 |
| 4 | 0.117 | 0 |
| 5 | 0.117 | 57.3 |
| 7 | 0.117 | 89.1 |
| 8 | 0.117 | 89.1 |
| 9 | 0.117 | 24.5 |
| 10 | 0.117 | 0 |
| 11 | 0.117 | 98 |
| 13 | 0.117 | 0 |

*Final concentration after dilution.

ASSAY II: Proton Transport across Lipid Membranes

This assay was used to judge the ability of protons to pass across vesicle membranes treated with glycosteroids. Vesicles loaded with carboxyfluorescein at non-self-quenching concentrations were prepared exactly as described above except that the carboxyfluorescein was added to the lipid mixture in 1 mL water (pH 6.5) at a concentration of 1 mM. After sonication under argon and rotary evaporation to remove the diethyl ether, the carboxyfluorescein-loaded vesicles were purified on a Sephadex-G25 column as described above. The concentration of the vesicle solution after purification on the G-25 column was adjusted until the fluorescent intensity equaled 100 after 100-fold dilution into 80 mM NaCl/5 mM Hepes buffer at pH 5.5.

A 100-fold dilution of the vesicle stock into pH 5.5 buffer was made immediately before each experiment and 1 mL of the diluted solution was put in a cuvette. To evaluate the ability of the glycosteroids to facilitate transport of protons across the lipid bilayer, 50 µL of a 0.245M solution of each glycosteroid in methanol was added to the 1 mL vesicle solution in a fluorescence cuvette and the change in fluorescent intensity was monitored over a period of 10 minutes. A significant decrease in fluorescence indicates that the glycosteroid in question facilitates the transport of protons across the membrane. This assay is based on the fact that the fluorescent intensity of carboxyfluorescein is much greater at pH 6.5 than at pH 5.5. If vesicles prepared at pH 6.5 are diluted into a buffer at pH 5.5, the fluorescent intensity will drop over time as the pH gradient across the membrane collapses.

As a control, 50 µL pure MeOH was added and the fluorescent intensity was found not to change significantly. Addition of MeOH at low concentrations therefore does not make the vesicles permeable to protons. The results are summarized in Table III.

TABLE III

| EX | Concentration (mM)* | % Decrease in Fluorescence |
|---|---|---|
| Triton-X 100 | 4.04 | 100 |
|  | 0.0116 | 2.43 |
| Gramicidin | 0.00579 | 87.2 |

TABLE III-continued

| EX | Concentration (mM)* | % Decrease in Fluorescence |
|---|---|---|
|  | 0.000579 | 81.6 |
| Cholic Acid | 0.0116 | 1.0 |
| Methyl Cholate | 0.0116 | 5.4 |
| Chenodeoxycholic Acid | 0.0116 | 8.2 |
| Deoxycholic Acid | 0.0116 | 5.39 |
| 1 | 0.0116 | 7.6 |
|  | 0.00579 | 4.3 |
| 2 | 0.0116 | 8.6 |
|  | 0.00579 | 1.7 |
| 3 | 0.0116 | 35.4 |
|  | 0.00579 | 21.0 |
| 4 | 0.0116 | 12.3 |
|  | 0.00579 | 7.89 |
| 5 | 0.0116 | 26.1 |
|  | 0.00579 | 19.4 |
| 7 | 0.0116 | 19.8 |
|  | 0.00579 | 15.2 |
| 8 | 0.0116 | 32.2 |
|  | 0.00579 | 20.6 |
| 9 | 0.0116 | 43.0 |
|  | 0.00579 | 27.4 |
| 11 | 0.0116 | 22.0 |
|  | 0.00585 | 14.7 |
| 13 | 0.0116 | 70.6 |
|  | 0.00579 | 35.2 |
|  | 0.000579 | 2.8 |

*Final concentration after dilution.

ASSAY III: The Antibiotic Efficacy of Erythromycin With and Without Enhancers

Erythromycin is an antibiotic whose efficacy is known to be increased by compounds that permeabilize cell membranes (Kubesch Pet al. Biochemistry (1987) 26:2139–2149). The efficacy of erythromycin, in the presence of novel glycosylated steroid derivatives of the present invention, was evaluated in a plate assay. Briefly, DH2 cells (a mutant strain of E. coli K-12, developed at Cold Spring Harbor Laboratories) grown in culture broth to an optical density (O.D.) of about 0.5 were mixed with 2.5 mL melted top agar (Top agar preparation: 10 grams tryprone (DIFCO), 5 grams yeast extract (DIFCO), 10 grams NaCl, 7 grams agar (DIFCO) and 1 mL 1M NaOH dissolved in one liter of pure water and autoclaved for 25 minutes) and then poured onto agar plates (agar plate preparation: 10 grams tryprone, 5 grams yeast, 10 grams NaCl, 15 grams agar, and 1 mL 1M NaOH dissolved in one liter pure water, autoclaved and cooled). After cooling for 15–30 minutes, each plate was divided into a grid and 4 µl of a test solution containing erythromycin (0.5 mM or 1.0 mM) in methanol, or erythromycin plus test compound (20 mM) in methanol, was spotted on each section of the grid. The plates were incubated for sixteen (16) hours at 37° C. and then examined for zones of inhibition (i.e., clear areas in sections of the grid where the test solution inhibited bacterial cell growth). Each section of the grid was scored. The section of the grid containing-erythromycin alone at 1.0 mM concentration was used as a standard for evaluating efficacy, with the other sections scored relative to this. The results, summarized in Table IV below show that 3α-O-p-methoxybenzoyl-cis-5,10-bis-α,α-7,12-glcosyl cholic acid methyl ester (referred to elsewhere herein as "CME") is the best "enhancer" in this assay. Of the non-glycosylated, bile acid derivatives used in this assay, only deoxycholic acid and its sodium salt showed any effect. Chenodeoxycholic acid and cholic acid and its salts did not have a detectable effect on the antibiotic efficacy of erythromycin in this assay. Interestingly, deoxycholic acid salts also have been shown to be more effective than chenodeoxycholic acid salts and cholic acid salts in enhancing the uptake of insulin through nasal membranes (Gordon GS et al. Proc. Nat'l. Acad. Sci. USA (1985) 82:7419–7423).

TABLE IV

| COMPOUND (20 mM) | ERYTHROMYCIN (mM) | EFFECT |
|---|---|---|
| Cholic Acid | 1.0 mM | — |
| Cholic Acid | 0.5 mM | — |
| Sodium Cholate | 1.0 mM | — |
| Sodium Cholate | 0.5 mM | — |
| Methyl Cholate | 1.0 mM | — |
| Methyl Cholate | 0.5 mM | — |
| Chenodeoxycholic Acid | 1.0 mM | — |
| Chenodeoxycholic Acid | 0.5 mM | — |
| Deoxycholic Acid | 1.0 mM | + |
| Deoxycholic Acid | 0.5 mM | + |
| Sodium Deoxycholate | 1.0 mM | + |
| Sodium Deoxycholate | 0.5 mM | + |
| CME | 1.0 mM | +++ |
| CME | 0.5 mM | +++ |
| 3α-O-benzoyl-trans-5,10-bis-α,α-7,12-glucosyl cholic acid methyl ester [BTME] | 1.0 mM | + |
| BTME | 0.5 mM | + |
| 3α-OH-cis-5,10-bis-α,α-glucosyl cholic acid K⁺ | 1.0 mM | + |
| 3α-OH-cis-5,10-bis-α,α-glucosyl cholic acid K⁺ | 0.5 mM | + |

—: erythromycin alone at 1.0 mM (baseline) and all lesser effects
+: enhancement relative to baseline
+++: significant enhancement relative to baseline The above plate assay was repeated using lower concentrations of CME and comparing its efficacy as an enhancer to that of the non-glycosylated parent, 3α-O-p-methoxybenzoyl-cis- 5,10-cholic acid methyl ester (the non-glycosylated form of CME and referred to elsewhere herein as "CDE"). The results, summarized in Table V below, show that while CME acts as an enhancer at very low concentrations, the non-glycosylated parent compound does not function as an enhancer. This demonstrates that the sugars are critical for enhancing effect.

TABLE V

| COMPOUND (mM) | ERYTHROMYCIN (mM) | EFFECT |
|---|---|---|
| 1.0 mM CDE | 0.1 mM | — |
| 0.1 mM CDE | 0.1 mM | — |
| 0.1 mM CME | 0.1 mM | + |
| 0.1 mM CME | 0.01 mM | + |
| 0.01 mM CME | 0.01 mM | + |
| 0.001 mM CME | 0.01 mM | + |
| 0.001 mM CME | 0.001 mM | — |

—: no detectable clearing (zone of inhibition)
+: visible clearing

ASSAY IV: EFFICACY OF ANTIFUNGAL AGENTS ON PROTOZOA WITH AND WITHOUT ADDED GLYCOSYLATED STEROID DERIVATIVES

CME, identified in both Assay I described above (compound 8 in the carboxyfluorescein assay) and in Assays II and III described above, as a good membrane permeabilizing agent, was tested for its ability to enhance the efficacy of two different antifungal agents on the protozoan *Crithidia fasciculate*. The ability of the non-glycosylated parent steroid to enhance efficacy was also studied. The studies were carried out as described in Pascal R A et al. *Biochemistry* (1983) 22:171–178 and Rahman M D et al. *J. Med. Chem.*

(1988) 31:1656–1659. Briefly, flasks containing 25 mL of growth medium (Preparation: 1.5 grams sucrose, 0.5 grams yeast extract, 0.4 grams tryptone and 0.25 mL triethanolamine dissolved in 100 mL water and pH adjusted to 8.0 with 10M HCl. Autoclave. After cooling, add 100 µL hemin (SIGMA) (2 mg hemin/1 mL 0.1N NaOH) and 20 mg. streptomycin sulfate (SIGMA)) and the antifungal agent and/or the glycosylated or nonglycosylated steroid derivatives were inoculated with aliquots of *C. fasciculate* (250 µL of culture containing approximately $1 \times 10^6 - 1 \times 10^7$ cells) (Preparation of culture: *C. fasciculate* in glycerol added to culture medium and grown, with shaking, for three (3) days at 26° C.; then stored at 0° to 4° C.). The cultures were incubated, with shaking, at 25° C. and growth was monitored by changes in absorbance at 535 nm (relative to the uninoculated medium).

Figure 2:
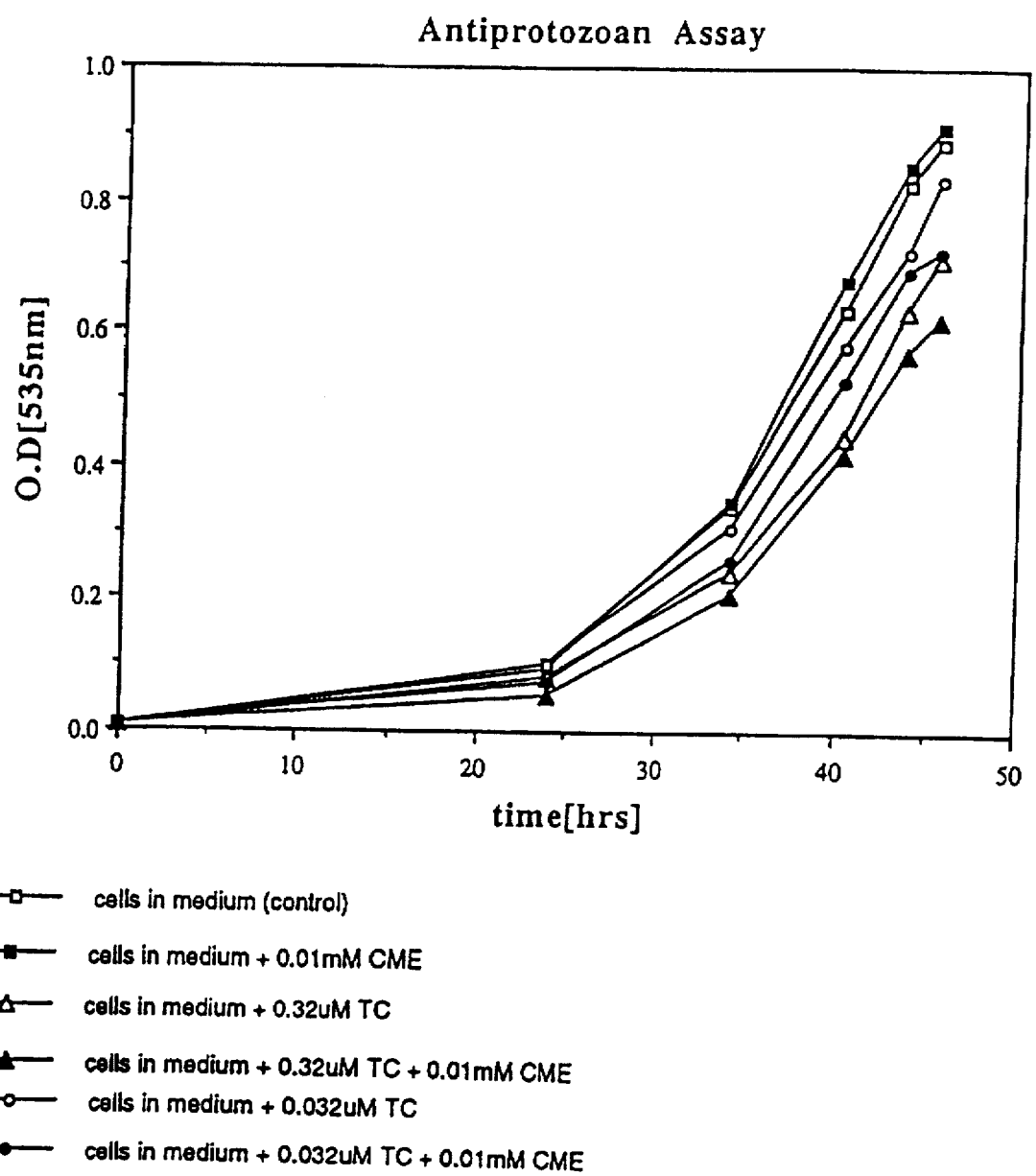
FIG. 2. A graph depicting the enhancing effect of CME, a novel glycosylated steroid derivative of the present invention, on the efficacy of thiacholestanol (TC), an antifungal agent.
Figure 3:
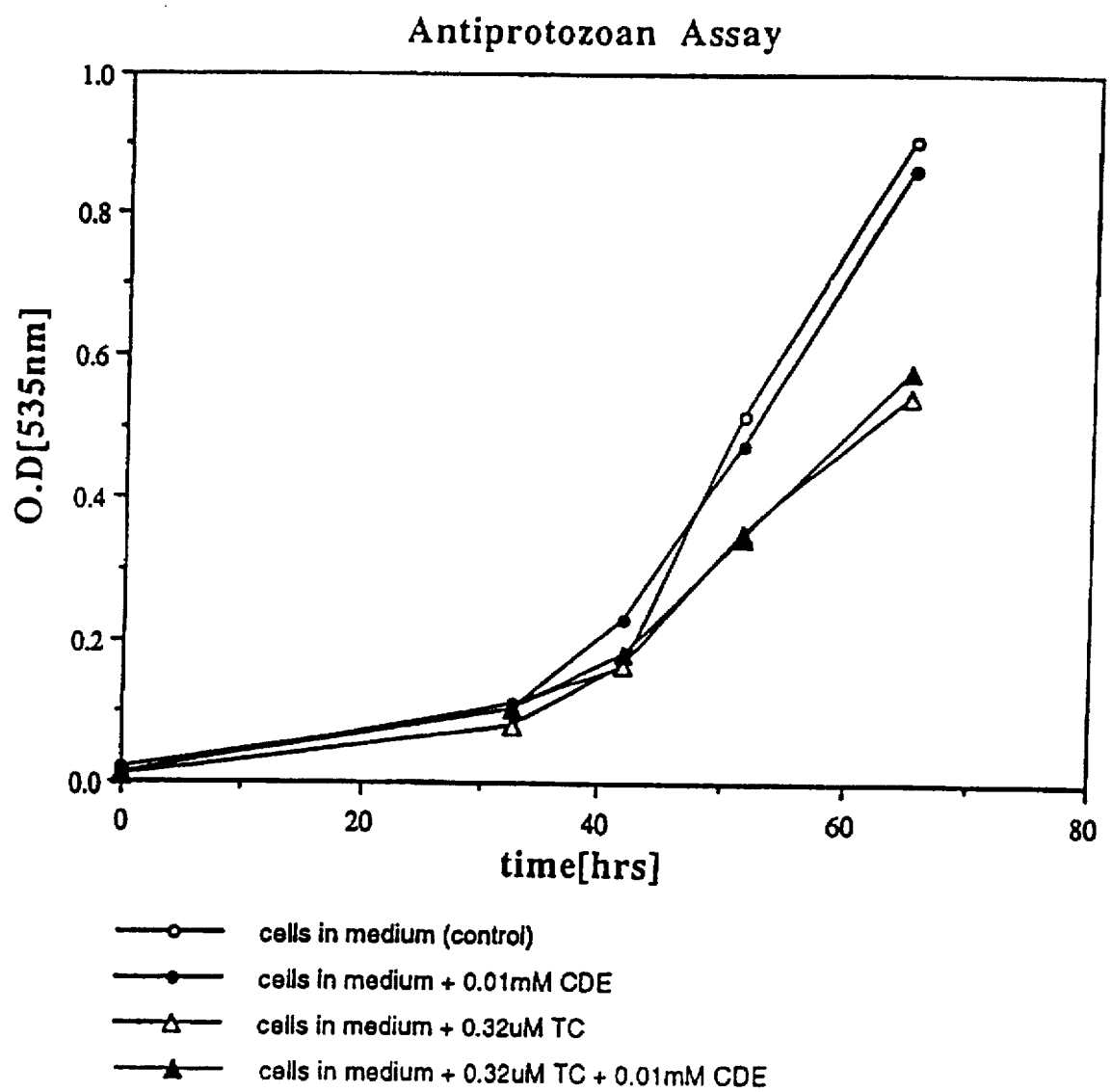
FIG. 3. A graph depicting the lack of an enhancing effect of CDE, the non-glycosylated version of CME, on the efficacy of thiacholestanol (TC), an antifungal agent.
Figure 4:
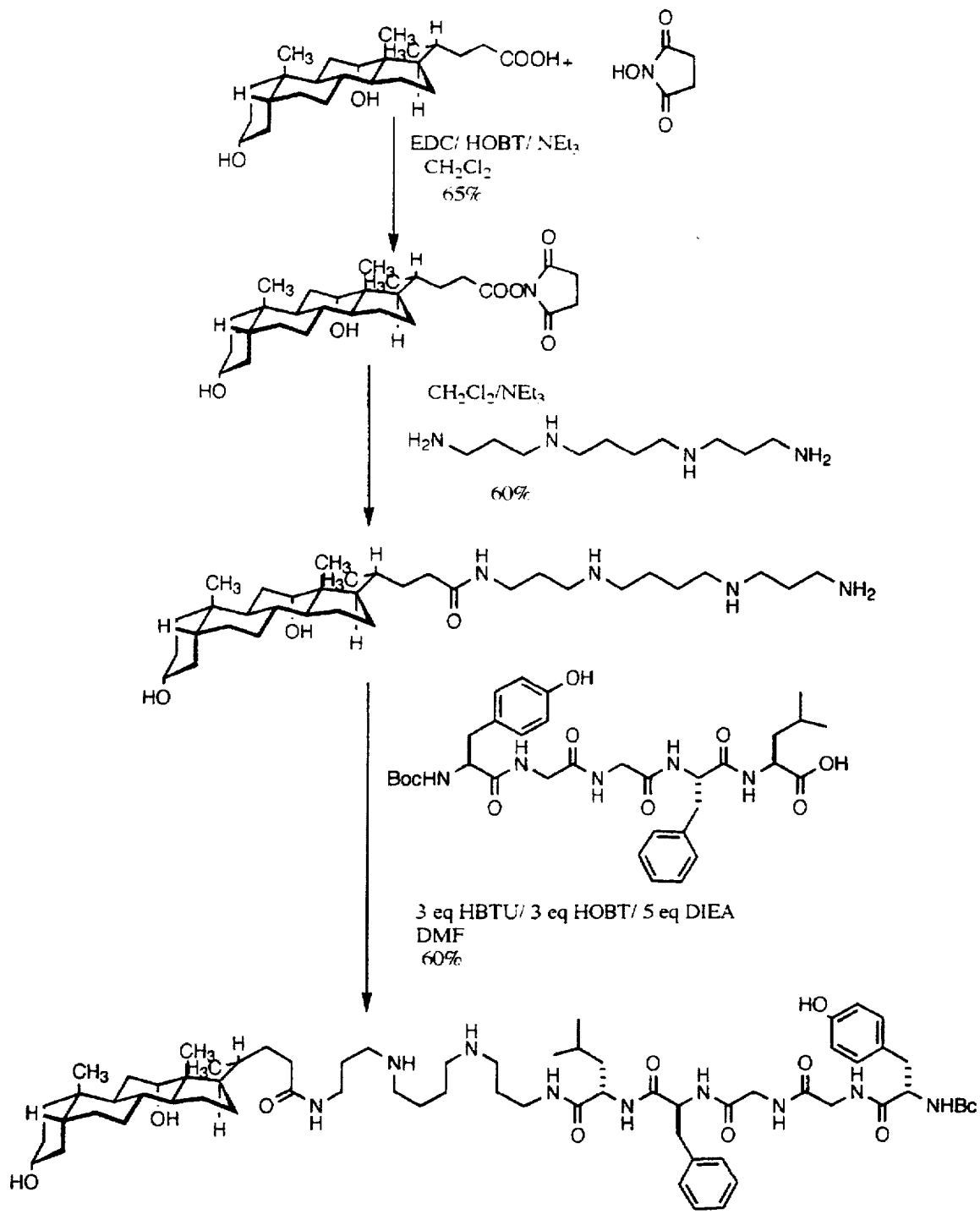
FIG. 4. Illustrates the synthetic scheme for the "synthetic" endorphins of the present invention.
Figure 5:
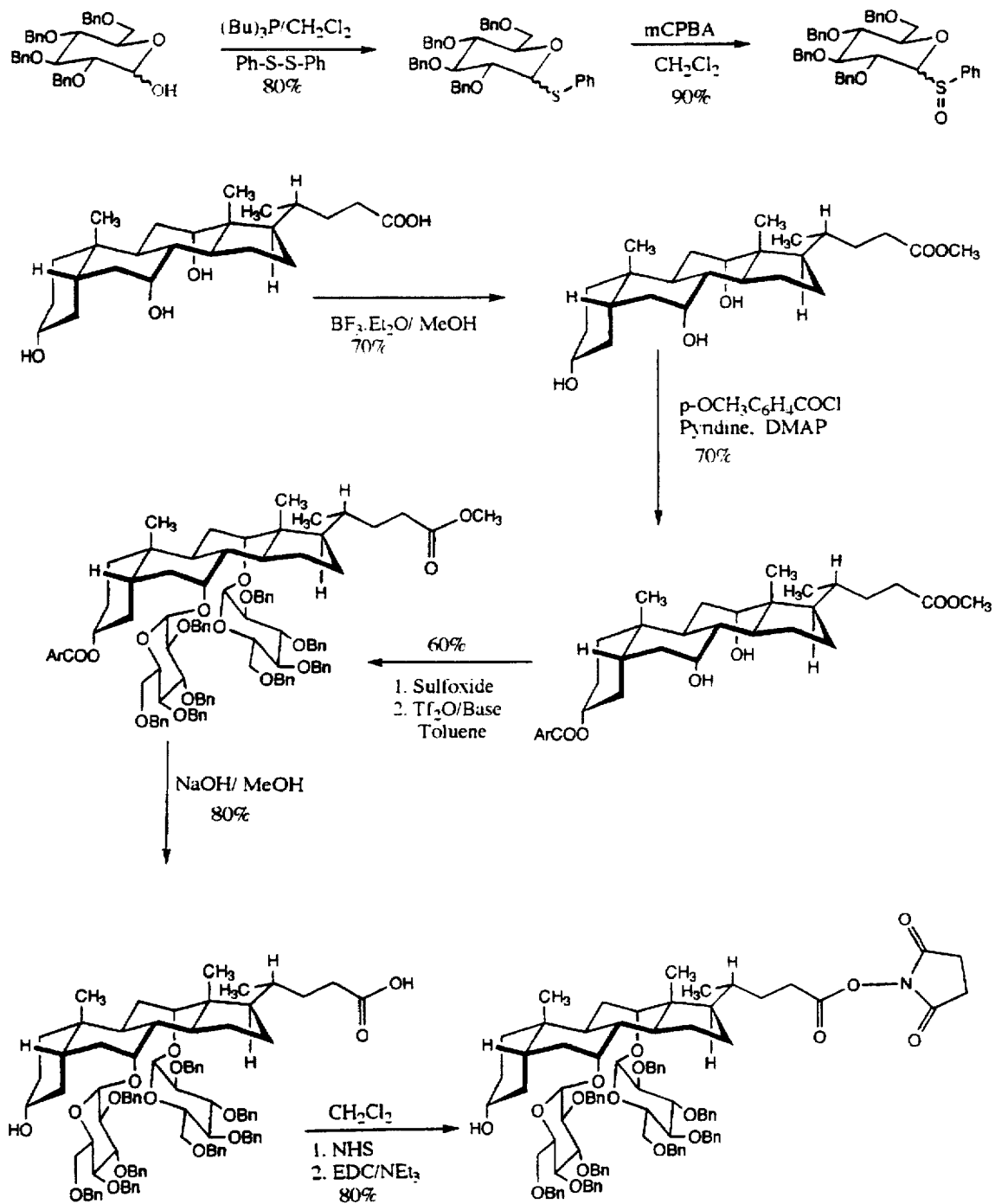
FIG. 5. Illustrates synthetic aspects of an endorphin mimic.
Figure 6:
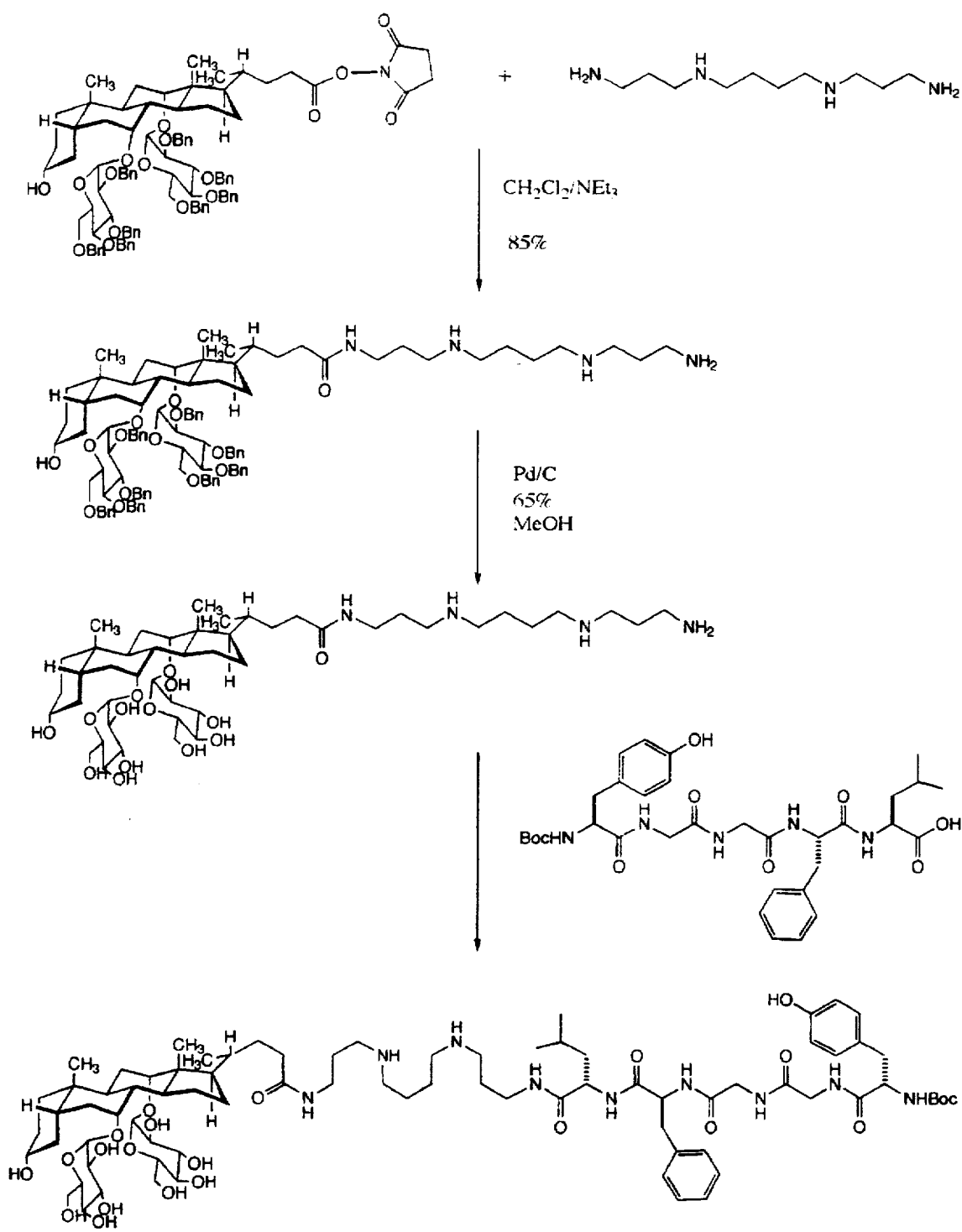
FIG. 6. Illustrates the continuation of the synthetic scheme for the preparation of an endorphin mimic.

Two different antifungal agents were used in the assays. The first was 10-thiastearic acid (10-TSA; see Rahman M D et al. *J. Med. Chem.* (1988) 31:1656–1659), which has an $IC_{50}$ of 10 µM; the second was 24thiacholestanol (24-TC; see Rahman M D et al. *J. Lipid Research* (1988) 29:1543–1548; Rahman M D and Pascal R A, *J. Biol. Chem.* (1990) 265:4989–4996), which has an $IC_{50}$ of 0.32 µM. The results, depicted in FIGS. 1, 2, and 3, demonstrate that the presence of CME enhances the efficacy of 10-TSA dramatically, allowing it to be used in 10- to 100-fold lower concentrations than otherwise necessary to achieve 50% inhibition of growth (FIG. 1). The presence of CME also was shown to enhance the efficacy of 24-TC (FIG. 2). The non-glycosylated parent steroid (CDE) was not observed to act as an enhancer in this assay (FIG. 3).

ASSAY V: EFFICACY OF DERIVATIVE-COMPOUND CONJUGATE ON THE PROTOZOA CRITHIDIA FASCICULATE

A novel glycosylated steroid derivative of Formula (I) is conjugated to a therapeutically-significant-compound by methods known in the art for coupling an acid group to an amine (i.e., to form an amide). The ability of the derivative-compound-conjugate to inhibit the growth of *Crithidia fasciculate* is evaluated as described in Pascal R A et al. *Biochemistry* (1983) 22:171–178 and Rahman M D et al. *J. Med. Chem.* (1988) 31:1656–1659. Briefly, flasks containing 25 mL growth medium alone, growth medium plus 24-TC at 0.32 µM concentration (the $IC_{50}$ level), and growth medium plus the derivative-compound-conjugate at 0.32 µM concentration are inoculated with aliquots of *C. fasciculate* (250 µL of culture containing approximately $1 \times 10^6 - 1 \times 10^7$ cells). The cultures are incubated with shaking at 25° C. and growth is monitored by changes in absorbance at 535 nm (relative to the uninoculated medium). Enhanced efficacy of the derivative-compound conjugate relative to the non-conjugated therapeutically-significant-compound would be reflected in a lower rate of growth (i.e., lower absorbance over time). The $IC_{50}$ level of the derivative-compound-conjugate can be measured by repeating the experiments with different concentrations of derivative-compound-conjugate to define the concentration that causes a 50% inhibition of growth relative to the culture containing *C. fasciculate* alone.

In another set of experiments, the flasks of growth medium contain derivative-compound-conjugate at its $IC_{50}$ value, as defined in the above experiments, plus a glycosylated steroid of the present invention, such as CME, which is known to increase the efficacy of 24-TC when not conjugated (hereinafter referred to as "the enhancer"). The enhancer is present at the following ratios relative to the derivative-compound conjugate: 0:1, 0.1:1, 1:1, 10:1, 100:1, 1000:1, or any concentration in between. The medium is inoculated with aliquots of *C. fasciculate* as described above and growth is monitored by changes in the absorbance at 535 nm relative to the uninoculated medium. Increased efficacy of the derivative-compound-conjugate in the presence of the enhancer is reflected in a lower rate of growth relative to the derivative-compound-conjugate alone. The optimum ratio of enhancer: derivative-compound conjugate is defined as that ratio which gives the lowest rate of growth.

The above-described examples serve merely to illustrate certain aspects of the present invention and should not be construed to limit the invention in any way. Other embodiments of the present invention should be apparent to those of ordinary skill having considered the descriptions provided herein. Such other embodiments, including their equivalents, are considered to fall within the scope and spirit of the present invention, which is limited solely by the following claims.

What is claimed is:

1. A conjugate comprising a 3β-amino-7α,12α-di-(1'-α-glucosyl)-5β-cholic acid, its salt, ester or amide covalently linked directly or via a linker (or spacer) group to a second compound attached to C3 or the C17-side chain.

2. The conjugate of claim 1 in which said second compound is covalently linked to C3 via the 3β-amino group.

3. The conjugate of claim 1 in which said second compound is covalently linked to the C17 side chain via the carboxylate, ester, or amide group.

4. A conjugate comprising a cholic acid or its analog selected from the group consisting of cholic acid, 3β-amino-5β-cholic acid, deoxycholic acid, chenodeoxy cholic acid, 3-deoxycholic acid, its salt, ester, or amide covalently linked directly or via a linker (or spacer) group to a second compound attached to C3 or the C17 side chain.

5. The conjugate of claim 4 in which said second compound is covalently linked to C3 via the substituent A, if present.

6. The conjugate of claim 4 in which said second compound is covalently linked to the C17 side chain substituent $R^5$.

* * * * *